(12) United States Patent
Palmer et al.

(10) Patent No.: US 8,959,038 B2
(45) Date of Patent: Feb. 17, 2015

(54) METHOD AND APPARATUS FOR MIMICKING HUMAN GAIT WITH PROSTHETIC KNEE DEVICES AND DETECTING WHEN STUMBLE RECOVERY IS NEEDED

(71) Applicant: Freedom Innovations, LLC, Irvine, CA (US)

(72) Inventors: Michael L. Palmer, Ladera Ranch, CA (US); Charles R. Bisbee, III, Mission Viejo, CA (US)

(73) Assignee: Freedom Innovations, L.L.C., Irvine, CA (US)

( * ) Notice: Subject to any disclaimer, the term of this patent is extended or adjusted under 35 U.S.C. 154(b) by 0 days.

(21) Appl. No.: 14/080,748

(22) Filed: Nov. 14, 2013

(65) Prior Publication Data

US 2014/0081423 A1   Mar. 20, 2014

Related U.S. Application Data

(62) Division of application No. 13/015,414, filed on Jan. 27, 2011, now Pat. No. 8,655,808.

(60) Provisional application No. 61/304,345, filed on Feb. 12, 2010.

(51) Int. Cl.
*G06F 15/18* (2006.01)
*A61F 2/64* (2006.01)
*A61B 5/11* (2006.01)
(Continued)

(52) U.S. Cl.
CPC ............... *A61F 2/64* (2013.01); *A61B 5/1114* (2013.01); *A61B 5/1117* (2013.01); *A61B 5/112* (2013.01); *A61B 5/1123* (2013.01); *A61F 2/68* (2013.01); *A61F 2002/701* (2013.01); *A61F 2002/704* (2013.01); *A61F 2002/7625* (2013.01); *A61F 2002/7645* (2013.01)
USPC ........................................................... 706/12

(58) Field of Classification Search
USPC ..................................................... 706/12, 45
See application file for complete search history.

(56) References Cited

U.S. PATENT DOCUMENTS 5,190,126 A    3/1993  Curnutt
6,113,642 A    9/2000  Petrofsky et al.
(Continued)

OTHER PUBLICATIONS

Wilkenfeld, Biologically Inspired Autoadaptive COntrol of a Knee Prosthesis, 2000, MIT, pp. 1-69.*

(Continued)

*Primary Examiner* — David Vincent

(57) ABSTRACT

The present invention relates to a prosthetic device including a prosthetic joint which accurately transitions between a loose mode and a stiff mode to more accurately mimic a human gait. The prosthetic joint includes a state controller which utilizes a sensor to detect prosthetic joint movement data, and compares it with prosthetic joint movement decision values to determine when a solenoid should be energized to place the prosthetic joint in the loose mode. An optimization unit connects to the prosthetic joint in a prosthetic joint system. The optimization unit generates a plurality of data files containing prosthetic joint movement data corresponding to an amputee walking without stumbling. By iteratively analyzing the prosthetic joint movement data, the optimization unit adjusts the prosthetic joint movement decision values to ensure that the prosthetic joint does not prematurely enter a stumble recovery state.

14 Claims, 18 Drawing Sheets

(51) Int. Cl.
*A61F 2/68* (2006.01)
*A61F 2/70* (2006.01)
*A61F 2/76* (2006.01)

(56) References Cited

U.S. PATENT DOCUMENTS

| | | |
|---|---|---|
| 6,978,872 B2 | 12/2005 | Turner |
| 2001/0029400 A1 | 10/2001 | Deffenbaugh et al. |
| 2002/0139203 A1 | 10/2002 | Chimura et al. |
| 2003/0033885 A1 | 2/2003 | Knox et al. |
| 2003/0120183 A1 | 6/2003 | Simmons |
| 2005/0154473 A1 | 7/2005 | Bassett |
| 2005/0283257 A1 | 12/2005 | Bisbee et al. |
| 2006/0136072 A1 | 6/2006 | Bisbee, III et al. |
| 2007/0050044 A1 | 3/2007 | Haynes et al. |
| 2007/0228500 A1 | 10/2007 | Shimazu et al. |
| 2007/0255424 A1 | 11/2007 | Leydet et al. |
| 2008/0139970 A1 | 6/2008 | Macomber et al. |
| 2008/0154156 A1 | 6/2008 | Dellon et al. |
| 2008/0295610 A1 | 12/2008 | Inamori |
| 2009/0030530 A1 | 1/2009 | Martin |
| 2009/0031822 A1 | 2/2009 | Ohta et al. |
| 2009/0054996 A1 | 2/2009 | Sykes et al. |
| 2009/0192619 A1 | 7/2009 | Martin et al. |
| 2010/0116277 A1 | 5/2010 | Lanfermann et al. |

OTHER PUBLICATIONS

PCT Application No. PCT/US2011/022752 International Search Report and Written Opinion, dated Sep. 1, 2011, 10 pages.
PCT Application No. PCT/US2011/022750 International Search Report and Written Opinion, dated Oct. 24, 2011, 9 pages.
Sup, Frank et al., "Design and Control of a Powered Transfemoral Prosthesis", The International Journal of Robotics Research, 2008, pp. 263-273, http://ijr.sagepub.com/cgi/content/abstract/27/2/263.
Wilkenfeld, A. J., "Biologically Inspired Autoadaptive Control of a Knee Prosthesis," Doctoral dissertation, 2000, Massachusetts Institute of Technology, pp. 1-69.
Au, S. et al., "Powered Ankle-foot Prosthesis to Assist Level-ground and Stair-decent gaits," Neural Networks, 21(4), 2008, pp. 654-666.
Blaya, J. A. et al., "Adaptive Control of a Variable-impedance Ankle-foot Orthosis to Assist Drop-foot Gait," Neural Systems and Rehabilitation Engineering, IEEE Transactions on, 12(1), pp. 24-31.

\* cited by examiner

```
8958 EXIT Weighted Swing Flexion--> LateSwin
    nMoment (128) < g.nMaxSwingMoment (140) -0.5*n Fire MomentDelta(2
**8983 Exit Swing Flexion-->WFExtend
    TimeSinceFire 177    AngPosition 707>nMaxSwingAngle 700

9667 EXIT WAITFOREXTEND-->ExtWait
    AngPosition (45)<nExtendedAngle(50)-3
9793 EXIT ExtendWait—WFHeeiload
    ExtendHoldTime (126)>gControlData.nExtendHoldDelay (125)
9794 Exit WAITFORHEELLOAD-->WFTrigger1
    nMoment -159<f.nHeelMin Max 3000
10063 EXIT WAITFORTRIGGER1-->WFPeak
    Moment(302) > T1(300)bRamp 0
10389 EXIT WAITFORPEAK-->WFTrigger2
    nMoment< nPeakMoment*0.97&&nMoment<nPeakMoment-25
Moment(879)
    Peak Momment(911)
10390EXITFORTRIGGER2-->MINFire Time
    Moment(874) < T2(2000)
10420 Exit Minimum Swing Time-->Waitbend
    TimeSinceFire 30
10499 EXIT Swing Terminal Stance-->EarlySwing
    bextended = 0
10500 EXIT Weighted Swing Flexion--> LateSwing
    nMoment (87) < g.nMaxSwingMoment (140) -0.5*g.nFireMomentDelta (25
8810595 Exit Swing Flexion-->WFExtend
    TimeSinceFire 205   AngPosition 707>nMax SwingAngle 700

11545 EXIT WAITFOREXTEND-->ExtWait
    AngPosition (46)<nExtendedAngle(50)-3
11671 EXIT EXTENDWAIT-->WFHelload
    ExtendholdTime (126)>g_ControlData.nExtendHoldDelay (125)
```

FIG. 17

METHOD AND APPARATUS FOR MIMICKING HUMAN GAIT WITH PROSTHETIC KNEE DEVICES AND DETECTING WHEN STUMBLE RECOVERY IS NEEDED

CROSS-REFERENCE TO RELATED APPLICATIONS

This application is a divisional application of U.S. patent application Ser. No. 13/015,414, filed on Jan. 27, 2011, which is hereby incorporated by reference in its entirety. This application and U.S. patent application Ser. No. 13/015,414 claim the benefit of U.S. Provisional Application Ser. No. 61/304,345, filed on Feb. 12, 2010. This application further incorporates by reference U.S. Pat. No. 7,655,050.

BACKGROUND

1. Field of the Invention

The present disclosure relates generally to prosthetic devices and, more particularly, to prosthetic devices including a prosthetic joint which more accurately transitions between a loose mode and a stiff mode to thereby more accurately mimic a human gait.

2. Description of the Related Art

Modern, computer-controlled prosthetic devices have many advantages over conventional prosthetic devices. For example, computer-controlled prosthetic devices can allow the amputees to walk with limited fear of stumbling or falling, allow amputees to lead a more active lifestyle, and improve the likelihood that amputees can realize their full economic potential. However, modern, computer-controlled prosthetic devices have some drawbacks, which may not allow amputees to take full advantage of all of their features.

For example, modern, computer-controlled prosthetic devices use an actuator, such as a hydraulic damping cylinder, which allows a prosthetic joint in the prosthetic device to be in a stiff mode or a loose mode. The transition between the stiff and loose mode is triggered by the occurrence of certain events (e.g., full extension of the prosthetic joint and reversal of the prosthetic joint's motion). However, the events that trigger the transition from stiff mode to loose mode, or vice versa, can occur at times when a transition is not desirable and thereby cause discomfort to the amputee.

For example, if the prosthetic joint is loose at the wrong time, the amputee could place weight on the prosthetic device and possibly lose his or her balance, or the amputee can feel the prosthetic joint loosen creating an undesirable sensation. However, if the prosthetic joint is stiff at the wrong time, the amputee may walk with an undesirable gait. Furthermore, since prosthetic devices often default to the stiff mode as a safety precaution (e.g. when the amputee stumbles), the transition from the stiff mode to the loose mode often does not occur when it should. This can reduce the amputee into walking in a manner similar to a peg-legged pirate when using the modern, computer-controlled prosthetic device. Given that the modern, computer-controlled prosthetic devices are designed to more accurately mimic a human gait and thus provide vastly more functionality than a crude peg, these drawbacks defeat the purpose of the modern, computer-controlled prosthetic devices and can limit their value.

To reduce such occurrences, variables controlling when the modern, computer-controlled prosthetic device enters stumble recovery can be adjusted. However, as the modern, computer-controlled prosthetic device becomes more sophisticated, the number of variables begins to increase drastically. Manually adjusting each variable to tune the modern, computer-controlled prosthetic device becomes laborious, time-consuming, and cost ineffective.

Thus, there is a need for a prosthetic joint which more accurately transitions between a loose mode and a stiff mode to thereby more accurately mimic a human gait.

SUMMARY

The present invention relates to a prosthetic device including a prosthetic joint which more accurately transitions between a loose mode and a stiff mode to thereby more accurately mimic a human gait. The prosthetic joint can include a state controller, a sensor system consisting of one or more sensors, a memory, and a controllable actuator system. The state controller can utilize the sensor system to detect prosthetic joint movement data, which is compared with expected normal prosthetic joint movement data to decide the state of the control system. When the prosthetic joint is in a Setup Swing Flexion state, the state controller progresses the prosthetic joint through additional states before commanding the actuator to place the prosthetic joint in a particular mode. This prevents the prosthetic joint from entering a mode prematurely. This can prevent for instance the amputee placing his weight on the prosthetic device and losing his balance. It can also prevent the amputee from feeling the prosthetic joint change resistance inappropriately and the subsequent undesirable sensation.

The prosthetic joint can also be part of a prosthetic joint system which also additionally includes an optimization unit. The optimization unit can generate a plurality of data files containing prosthetic joint movement data corresponding to an amputee walking at various speeds without stumbling. By iteratively analyzing the prosthetic joint movement data, the optimization unit can adjust the prosthetic joint movement decision values to ensure that the prosthetic joint does not prematurely enter a stumble recovery state. This ensures that the prosthetic joint does not prematurely enter high resistance mode due to a perceived stumble when the amputee is not actually stumbling. Optimizing the prosthetic joint movement decision values can also reduce instances where the prosthetic device unnecessarily transitions to the incorrect mode. Furthermore, it also allows for greater accuracy in transitioning into a high resistance mode when the amputee has an unexpected gait deviation. This can provide better support for the amputee. The optimization unit also allows for a simplistic optimization of the prosthetic joint movement decision values, reducing setup costs for the prosthetic device.

In one embodiment, the present invention is a prosthetic joint capable of selectively entering a stumble recovery state including a state controller configured to detect prosthetic joint movement data, determine a state of the prosthetic joint using the prosthetic joint movement data, and analyze the prosthetic joint movement data and a prosthetic joint movement decision values to determine when the state of the prosthetic joint should enter a stumble recovery state.

In another embodiment, the present invention is a method for controlling a state in a prosthetic joint including detecting, using a state controller, prosthetic joint movement data, determining, using a state controller, a state of the prosthetic joint using the prosthetic joint movement data, retrieving, using the state controller, prosthetic joint movement decision values, and analyzing, using the state controller, the prosthetic joint movement data and prosthetic joint movement decision values to determine when the state of the prosthetic joint should enter a stumble recovery state.

In yet another embodiment, the present invention is a prosthetic joint system including an optimization unit configured to generate a plurality of data files containing prosthetic joint movement data from a movement of a prosthetic joint capable of being in one or more states, and iteratively analyzing the prosthetic joint movement data for each of the plurality of data files to determine the prosthetic joint movement decision values to ensure a state of the prosthetic joint matches up with a corresponding movement of the prosthetic joint.

In still yet another embodiment, the present invention is a method of optimizing a prosthetic joint system to ensure a state of a prosthetic joint matches with a corresponding movement of a prosthetic joint including generating, using an optimization unit, a plurality of data files containing prosthetic joint movement data from a movement of a prosthetic joint, and iteratively analyzing, using the optimization unit, the prosthetic joint movement data for each of the plurality of data files to determine the prosthetic joint movement decision values to ensure a state of the prosthetic joint matches up with a corresponding movement of the prosthetic joint.

BRIEF DESCRIPTION OF THE DRAWINGS

Embodiments of the present disclosure will now be described, by way of example only, with reference to the following drawings in which:

FIG. 17 depicts state transitions identified by the optimization unit according to an embodiment of the present invention;

DETAILED DESCRIPTION

Figure 1:
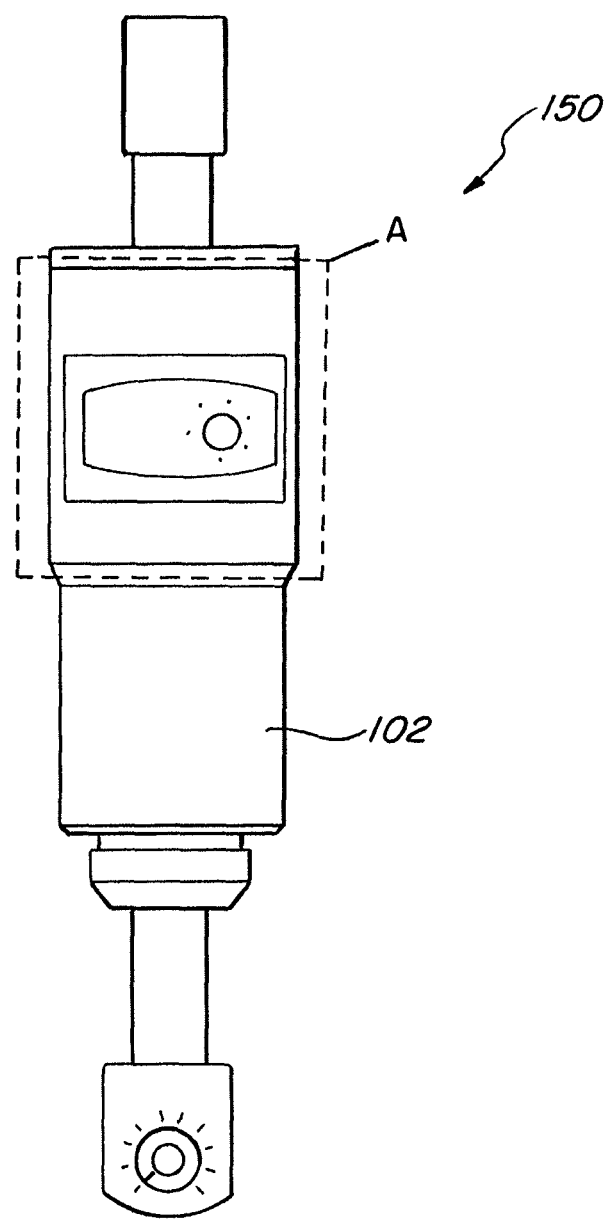
FIG. 1 depicts a hydraulic cylinder that actuates a prosthetic joint according to an embodiment of the present invention.
Figure 3:
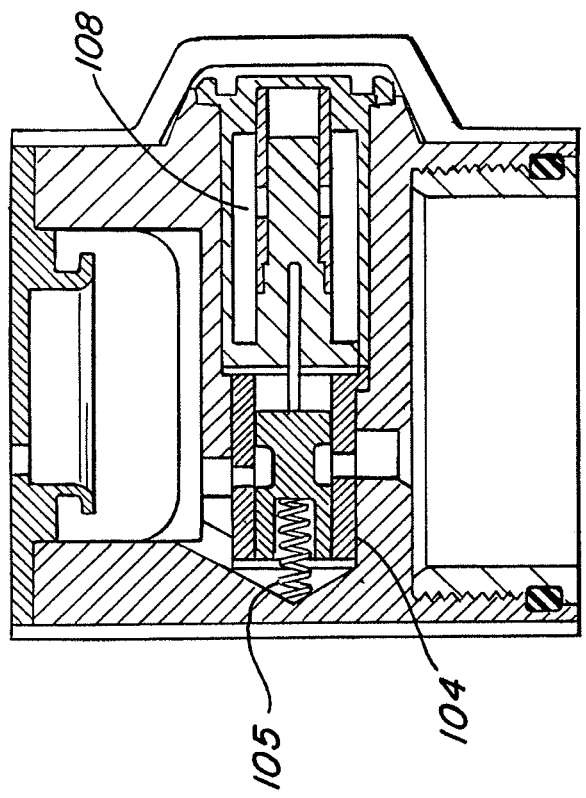
FIG. 3 depicts a section view of a portion of the hydraulic cylinder according to an embodiment of the present invention.
Figure 2:
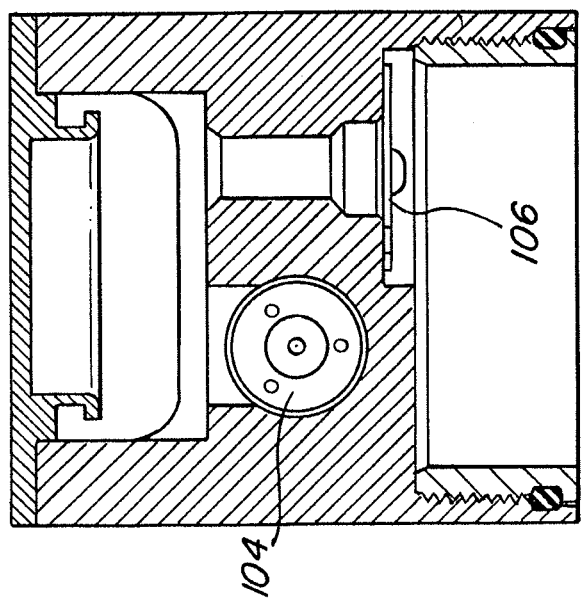
FIG. 2 depicts a section view of a portion of the hydraulic cylinder according to an embodiment of the present invention.

In one embodiment, the present invention includes, for example, an actuator 150. The actuator 150 can be part of a prosthetic joint, which in turn can be used as part of a prosthetic device. The actuator 150 includes, for example, a hydraulic damping cylinder 102. As seen in FIG. 2 (which is a cross-sectional view of the portion A in FIG. 1, the hydraulic damping cylinder 102 includes a spool valve 104 and reed check valve 106. As seen in FIG. 3, the hydraulic damping cylinder 102 also includes a return spring 105 and a solenoid 108.

When the solenoid 108 is energized, the solenoid 108 opens the spool valve 104 and permits fluid to flow through the spool valve 104. This reduces the damping of the hydraulic damping cylinder 102 to permit easy bending of the prosthetic joint 100. However, when the solenoid 108 is de-energized, the spool valve 104 can be closed by return spring 105, and no fluid flows through the spool valve 104. This increases the damping of the hydraulic damping cylinder 100. Thus, the hydraulic damping cylinder 102, and the actuator 150 operate in a binary operation: stiff mode (with increased damping and high resistance) and loose mode (with decreased damping and low resistance) depending on what portion of the gait cycle the amputee is in.

Figure 4:
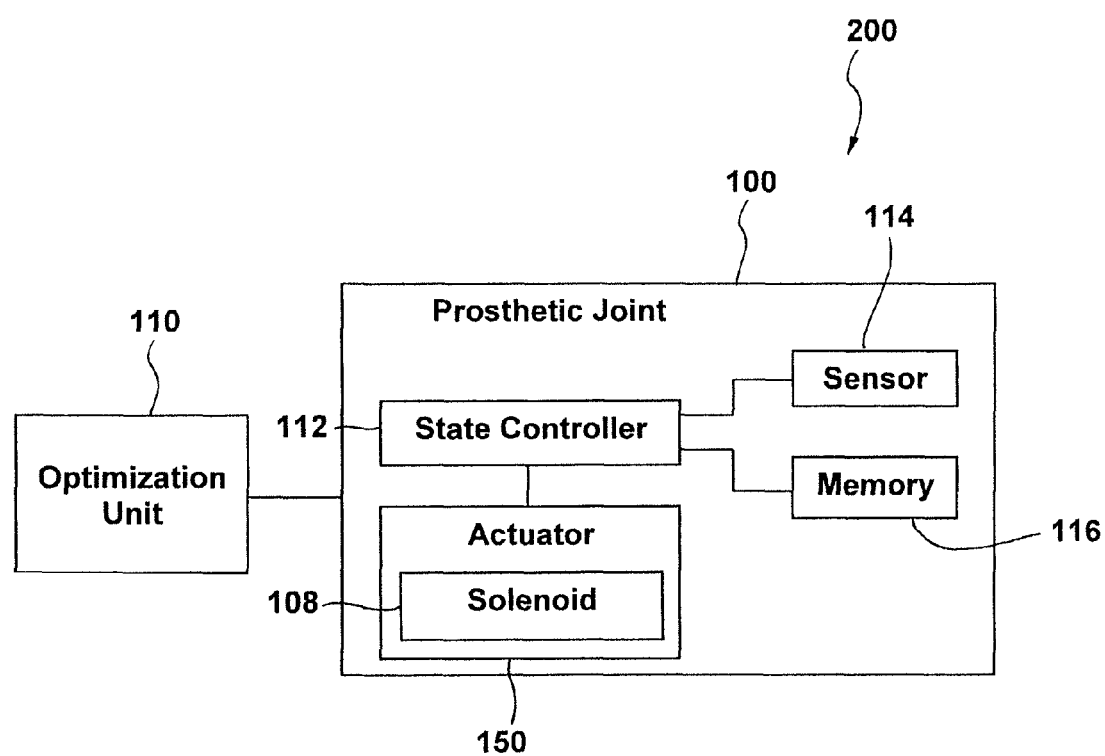
FIG. 4 is a box diagram of a prosthetic joint system according to an embodiment of the present invention.

As seen in FIG. 4, the actuator 150 can be part of a prosthetic joint 100 and a prosthetic joint system 200. Thus, the prosthetic joint 100 can also operate in a binary operation: stiff mode (with increased damping) and loose mode (with decreased damping) depending on what portion of the gait cycle the amputee is in. The prosthetic joint system 200 can include the prosthetic joint 100, and an optimization unit 110. The prosthetic joint 100 can also include a state controller 112 connected to the solenoid 108 in the actuator 150, a sensor 114 connected to the state controller 112, and a memory 116 connected to the state controller 112. The state controller 112 energizes or de-energizes the solenoid 108 based on prosthetic joint movement data detected by the sensor 114 and prosthetic joint movement decision values stored in the memory 116. Thus, the state controller 112 can utilize the sensor 114 to detect the prosthetic joint movement data. The prosthetic joint movement data are related to the movement of the prosthetic joint 100 and/or the prosthetic device. In one embodiment, the prosthetic joint movement data can include, for example, swing time data, moment data, knee angle data, and/or knee angle rate of change data.

In the current but not the only possible embodiment of this invention, the prosthetic joint movement data decision values can include, for example, the straight knee angle decision value (ExtendedAngle−3), the bent knee angle decision value (ExtendedAngle+3), the extend wait state time delay (ExtendHoldDelay), the heel moment decision value (HeelMinMax), rising moment decision value (T1), wait for trigger 1 state count (MaxHeelWait), declining peak moment decision value (PeakMoment−25 or PeakMoment*0.95), declining moment decision value (T2), maximum leg swing time (sdt), maximum knee angle (MaxSwingAngle), maximum knee angle rate of change (MaximumSwingRate), minimum swing state time delay (MinFireTime), bent knee time decision value (SwingBendTime), first moment boundary value (MinMoment+FireMomentDelta), moment noise buffer value (FireMomentDelta), second moment boundary value (MaxSwingMoment+FireMomentDelta), maximum swing moment value (MaxSwingMoment), decreased moment time decision value (SwingBendTime+SwingUnloadTime), decreased moment time buffer value (SwingUnloadTime), third moment boundary value (MinSwingMoment+FireMomentDelta), minimum swing moment boundary (MinSwingMoment), maximum swing moment (MaxSwingMoment), angle peak noise buffer value (AngPeakDelta), and/or the minimum knee angle rate of change value (MinSwingRate). The prosthetic joint movement data decision values can aid in the operation of the prosthetic joint 100 and will be described in more detail later.

The state controller 112 determines which state the prosthetic joint 100 should be in, in order to ensure that the hydraulic damping cylinder 102 and the prosthetic joint 100 are in the correct state that corresponds to the gait of the user. The state of the hydraulic damping cylinder 102 and/or the prosthetic joint 100 indicates whether the amputee is progressing through a normal gait and also whether the hydraulic damping cylinder 102 and the prosthetic joint 100 is in a stiff mode or a loose mode.

Figure 5:
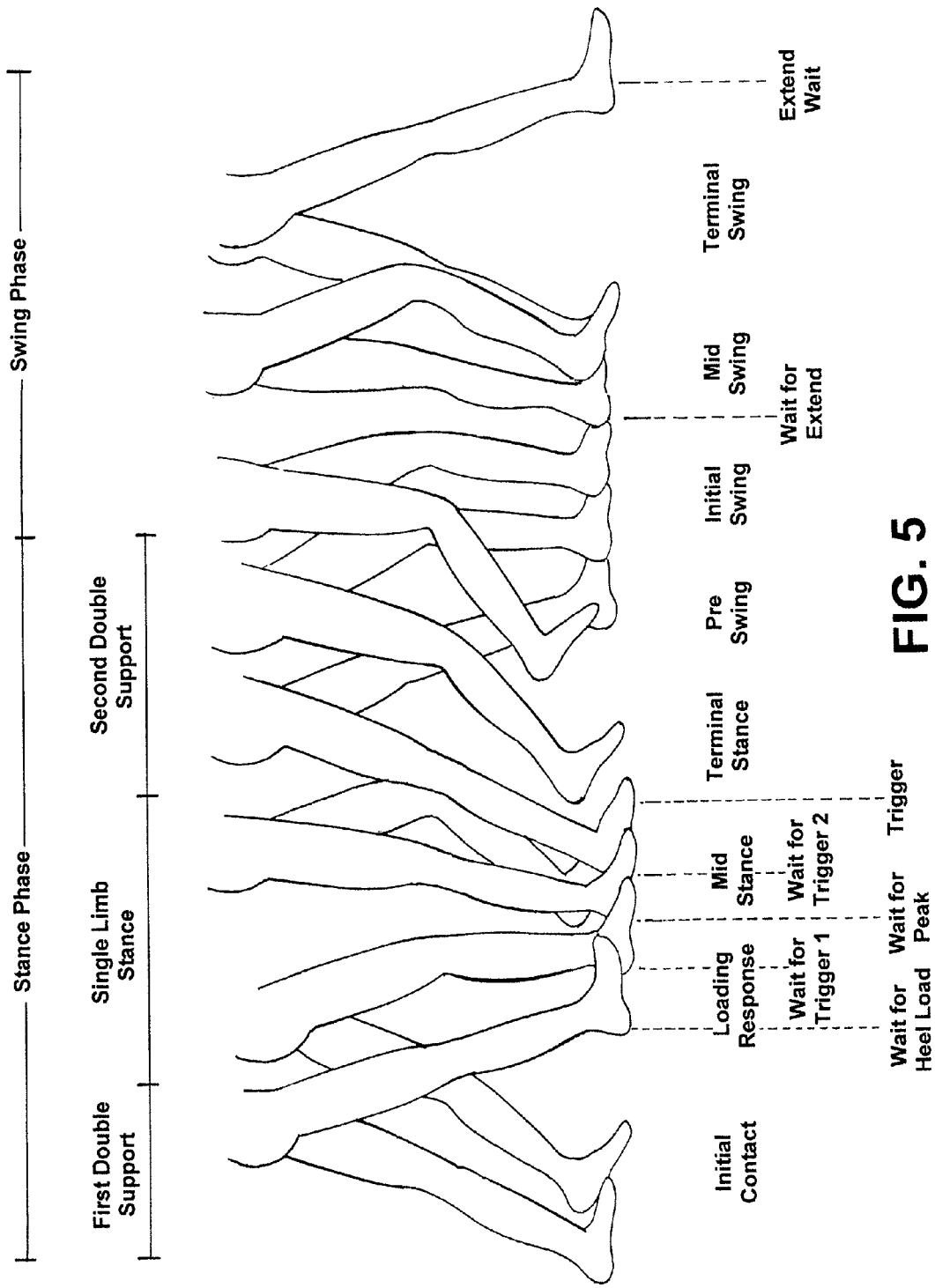
FIG. 5 depicts an exemplary gait cycle and corresponding states of a prosthetic joint according to an embodiment of the present invention.

As seen, for example, in FIG. 5, for each leg, a walking gait can be divided into two phases, a stance phase and a swing phase. The stance phase is defined as the period of time during which the foot of the observed leg is weighted. The swing phase is defined as the period of time when the foot of the observed leg is un-weighted. Within the stance phase are multiple sub-phases such as the initial contact sub-phase, the loading response sub-phase, the mid stance sub-phase, the terminal stance sub-phase, the pre swing sub-phase, the initial swing sub-phase, the mid-swing sub-phase, and/or the terminal swing sub-phase.

The stance phase of a walking gait begins as the heel strikes the ground, indicated by the sub-phase initial contact. Upon heel strike, the knee flexes slightly to absorb some of the impact forces acting on the limb due to weight acceptance as indicated by the leading response sub-phase.

After the foot is flat on the ground, the shin begins to rotate forward about the ankle as indicated by the mid stance sub-phase. During the mid stance, the shin rotates, and the knee remains flexed in order to minimize the rise of the person's center of mass as it passes over the ankle joint center. As the shin continues to rotate forward and the center of mass progresses forward, the weight acting on the limb moves towards the toe of the foot. The force of the weight acting on the toe generates a torque about the knee joint that tends to straighten, or extend, the knee—referred to as "stance extension" of the knee. Stance extension continues until the transition point to the swing phase.

Soon after the knee is completely extended, the toe pushes off the ground, as indicated by the terminal stance sub-phase. As the toe pushes off the ground, the knee begins to flex as indicated by the pre swing sub-phase. The knee flexes to about 60° degrees in the initial swing sub-phase. In order to keep the toe from stubbing on the ground, the knee will remain flexed as the leg rotates, or swings, forward about the hip joint in the initial swing sub-phase. As the leg continues to swing forward the knee will begin to extend until it is nearly straight—referred to as "swing extension" of the knee during the mid swing sub-phase. Soon after the knee is fully extended in the terminal swing sub-phase. Thereafter, the heel of the foot will strike the ground again, and the gait cycle begins all over.

During the level-ground walking gait cycle described above, a biological knee, together with the muscles acting on it, functions primarily as an absorber of energy. Thus, to mimic a natural walking gait and to support the amputee, the hydraulic damping cylinder 102 provides a relatively high amount of resistance to motion, or damping, making the prosthetic joint 100 comparatively stiff and able to support high forces. However, at certain times, the hydraulic damping cylinder 102 provides a relatively low resistance making the prosthetic joint 100 comparatively loose and able to swing freely to facilitate the natural gait of the amputee. For example, the prosthetic joint 100 should be loose during portions of the terminal stance sub-phase, the pre swing sub-phase, and the initial swing sub-phase. However, even in those sub-phases, the prosthetic joint 100 may become stiff when there is abnormal gait event, such as when the amputee is falling or stumbling.

Based on the movements of the amputee in the normal gait cycle, the state controller 112 controls whether the prosthetic joint 100 should be stiff or loose to both facilitate the normal gait of the amputee and also to aid the amputee when the amputee is falling or has an abnormal gait. To do so, the state controller controls which state the prosthetic joint 100 is in. As seen in FIG. 5, the prosthetic joint 100 is in generally one of 7 states during a natural gait: Wait for Heel Load (phase 3) state, Wait for Trigger 1 (phase 4) state, Wait for Peak (phase 5) state, Wait for Trigger 2 (phase 6) state, Triggered (phase 7) state, Wait for Extend (phase 1) state, and Extend Wait (phase 2) state. Generally the state controller 112 starts the prosthetic joint 100 at the Wait for Extend (phase 1) state and progresses through the states unless there are any abnormalities, in which case the state controller 112 returns the state of the prosthetic joint 100 to the Wait for Extend (phase 1) state.

Figure 6:
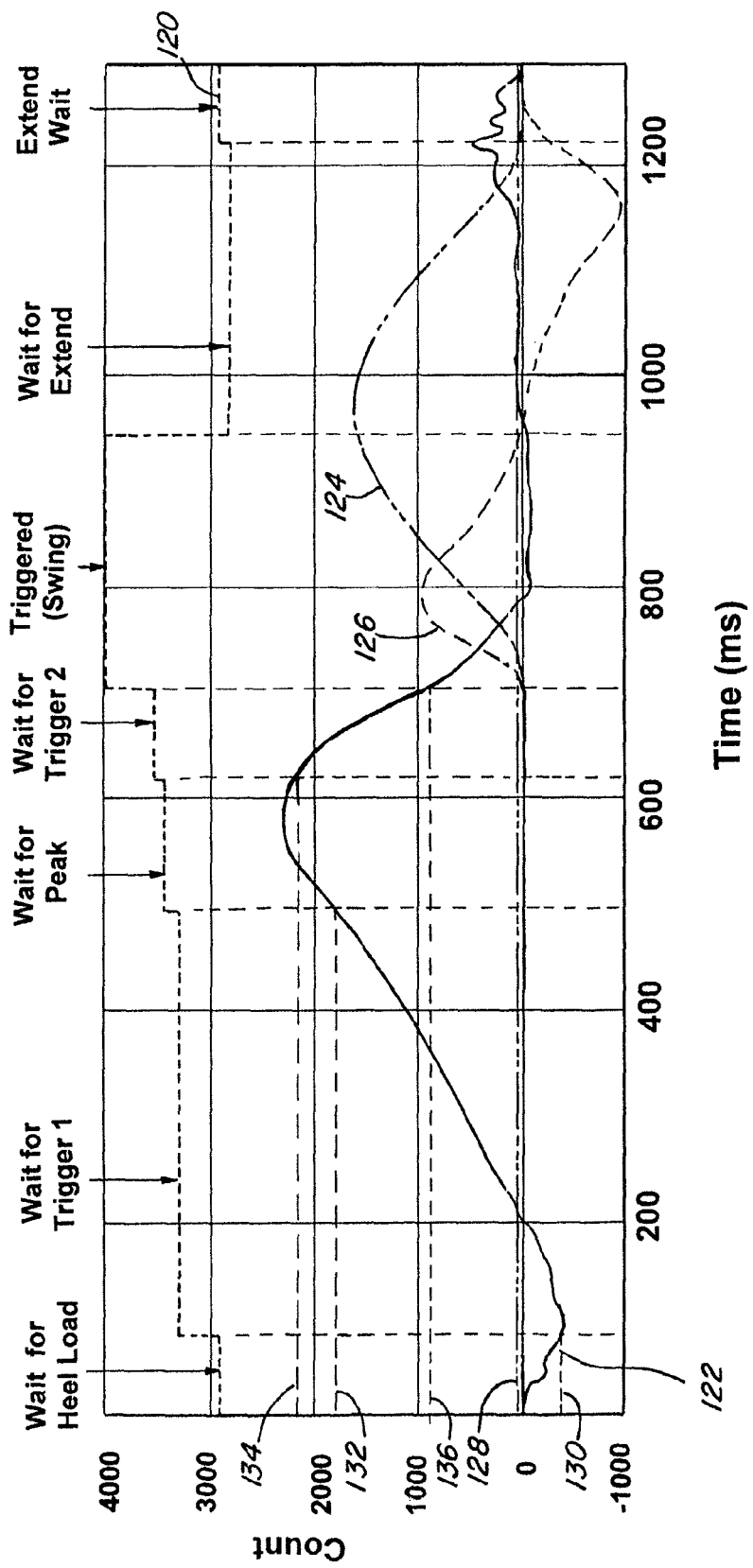
FIG. 6 is a graph of sagittal plane moment data, knee angle data, and knee angle rate of change data for an exemplary gait cycle and corresponding states of a prosthetic joint according to an embodiment of the present invention.
Figure 7:
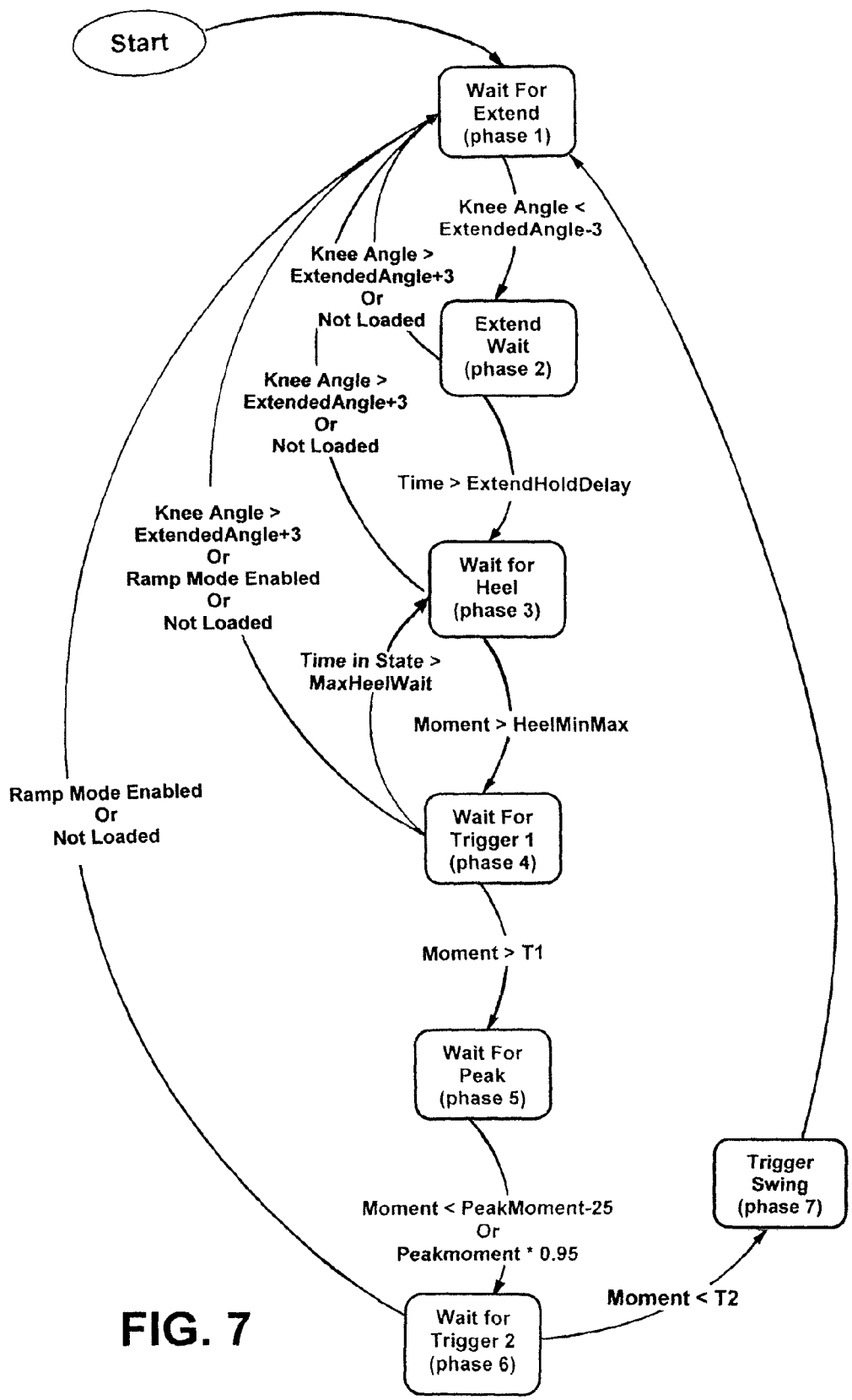
FIG. 7 is a flowchart of states of a prosthetic joint according to an embodiment of the present invention.

The gait cycle and the states of the prosthetic joint 100 can be seen with reference to FIGS. 6 and 7. FIG. 6 depicts the state of the prosthetic device along with the corresponding prosthetic joint movement data such as moment data, the knee angle data, and the knee angle rate of change data. In FIG. 6, the moment data is indicated by the curve 122, the knee angle data is indicated by the curve 124, and the knee angle rate of change data is indicated by the curve 124. FIG. 7 is a flow chart depicting the flow path of the states of the prosthetic joint 100 as controlled by the state controller 112 in one possible embodiment of the current invention. In FIG. 7, each circular or rectangular shape represents a state and the arrows represent allowable state transitions. The text in the state (circular or rectangular shape) names the state. The text along any arrow shows the conditions that govern the transition. The arrow is followed if the condition is true. Staying in the same state is not shown and is implied. So in any control cycle the state can remain the same or change by following one of the arrows.

The normal sequence of states flows from top to bottom on each page. The desired level ground walking transitions are all downward and exit the bottom of a state and reiterates to the top. Abort or stumble recovery is indicated by upward transitions to the Wait for Extend (phase 1) state. The prosthetic joint movement decision values control most of the state transitions. The prosthetic joint movement decision values can be optimized or varied by the user or the optimization unit 110, which will be discussed later.

Although in FIG. 5, the Wait for Heel Load (phase 3) state is depicted on the left most side, the state controller 112 sets the default state for the prosthetic joint 100 to be the Wait for Extend (phase 1) state, as shown in FIGS. 6 and 7. Thus, each cycle begins at the Wait for Extend (phase 1) state and ends at the Triggered (phase 7) state when the state controller 112 causes the solenoid 108 to be energized. Of course, after the Triggered (phase 7) state, the state of the prosthetic joint 100 transitions back to the Wait for Extend (phase 1) and the cycle is repeated.

Wait for Extend (Phase 1):

In one embodiment, this is the starting state of the prosthetic joint 100. In the Wait for Extend (phase 1) state, the state controller 112 waits until the prosthetic joint 100 is extended past a knee angle threshold. In FIG. 7, a fully straightened knee has an angle of 0°, thus as the value of the knee angle decreases, the prosthetic joint 100 is straightening out. When it has a value below an extended knee angle decision value, indicated by ExtendedAngle−3 in FIG. 7, the prosthetic joint 100 is considered to be extended and proceeds to the next state, Extend Wait (phase 2). In FIG. 6, the knee angle decision value Extended Angle−3 is indicated by the line 128.

The Wait for Extend (phase 1) state is also, for example, a stumble recovery state. This is because in the Wait for Extend (phase 1) state, the prosthetic joint 100 is set to be stiff and the amputee can exit the state by extending the prosthetic joint 100, signifying that the amputee is in control of his movements and ready for a normal gait.

Extend Wait (Phase 2):

The prosthetic joint 100 is in an Extend Wait (phase 2) state for a predetermined period of time, such as an extend wait state time delay. In FIG. 7, the extend wait state time delay is indicated as ExtendHoldDelay. Thus, the Extend Wait (phase 2) state implements a time delay to prevent noise from falsely triggering the prosthetic joint 100 into swing. For example, as seen in FIG. 6, there is some jitter in the moment data while the prosthetic device is in the Extend Wait (phase 2) state. The extend wait state time delay ExtendHoldDelay has a default value of 125 ms, but can be adjusted during the setup of the prosthetic joint 100. The normal exit is at the expiration of this time.

This means that the prosthetic joint 100 must remain in the extended position for this time. If the prosthetic joint 100 does not remain extended for this period of time, the state controller 112 returns the state of the prosthetic joint 100 to the Wait for Extend (phase 1) state to allow the prosthetic joint 100 to remain in a stiff state. Furthermore, if the knee angle data indicates that the prosthetic joint 100 is bent beyond a bent knee angle decision value ExtendedAngle+3, then the state controller 112 also returns to the Wait For Extend (phase 1) state. This is because the prosthetic joint 100 is being bent when it should be extended, signifying that there is an abnormal gait.

In addition, the Extend Wait (phase 2) state can also exit to the Wait for Extend (phase 1) state when a Not Loaded condition is reached. In a Not Loaded condition, the moment data indicates that the moment of the prosthetic joint 100 is substantially near zero (0) for a predetermined period of time. The predetermined period of time ensures that the Not Loaded condition is not triggered just when the moment crosses the zero moment boundary, but instead is triggered when the moment hovers around zero for some period of time. Depending on the data used, however, the predetermined period of time is optional and can be eliminated if the moment will not cross the zero moment boundary such as if load data is used.

Wait for Heel Load (Phase 3):

In the Wait for Heel Load (phase 3) state, the state controller 112 looks for a heel moment less than a heel moment decision value. Heel moments are seen as negative moments, thus the lower the value, the greater the moment exhibited when the heel strikes the ground. The state controller 112 transitions the prosthetic joint 100 to the next state when the moment data indicates that the moment is below the heel moment decision value HeelMinMax. The heel moment decision value HeelMinMax is indicated by the line 130 in FIG. 6. When the moment falls below the heel moment decision value HeelMinMax, the state controller 112 transitions the state of the prosthetic joint 100 to the Wait for Trigger 1 (phase 4) state. Normally HeelMinMax is set to a high moment value, so the state controller 112 transitions out of the Wait for Heel Load (phase 3) state quickly. An abnormal exit occurs when the prosthetic joint 100 bends as indicated by the knee angle being greater than the bent knee angle decision value ExtendedAngle+3. In such a case, the state controller 112 returns the state of the prosthetic joint 100 to the Wait for Extend (phase 1) State due to an abnormal gait. In addition, the Wait for Heel Load (phase 3) state can also exit to the Wait for Extend (phase 1) state when the Not Loaded condition is reached.

Wait for Trigger 1 (Phase 4):

In the Wait for Trigger 1 (phase 4) state, the state controller 112, waits for the moment to rise above a rising moment decision value T1 as indicated by the line 132 in FIG. 6. The rising moment decision value T1 is typically set to two-thirds (⅔) of the peak moment occurring during a normal step, but can be adjusted as necessary during setup of the prosthetic joint 100. When the moment data indicates that the moment is greater than the rising moment decision value T1, the state controller 112 sets the state of the prosthetic joint 100 to the Wait for Peak (phase 5) state.

However, once the state controller 112 determines that the state of the prosthetic joint 100 is in the Wait for Trigger 1 (phase 4) state, the state controller 112 initiates a wait for trigger 1 count. The wait for trigger 1 count is based on a timer which measures the time that the prosthetic joint 100 is in the Wait for Trigger 1 (phase 4) state. When the wait for trigger 1 count exceeds the maximum heel wait time decision value, which is shown as the MaxHeelWait value in FIG. 7, the state controller 112 returns the state of the prosthetic joint 100 back to the Wait for Heel Load (phase 3) state.

If the knee bends beyond the bent knee angle decision value ExtendedAngle+3, the state controller 112 returns the state of the prosthetic joint 100 back to the Wait For Extend (phase 1) state. In addition, the Wait for Trigger 1 (phase 4) state can also exit to the Wait for Extend (phase 1) state when the Not Loaded condition is reached. The Wait for Trigger 1 (phase 4) state can also exit to the Wait for Extend (phase 1) state when a Ramp Mode is Enabled indicating that the amputee is traversing an incline, such as when he is walking down relatively steep steps, a hill, or a ramp.

Wait for Peak (Phase 5):

In the Wait for Peak (phase 5) state, the state controller 112 analyzes the moment data to determine when the moment has reached the peak moment and has started declining. For example, the state controller 112 analyzes the moment data to determine that the peak moment has been reached, and furthermore that the moment data indicates that the moment has declined below a declining peak moment decision value.

The declining peak moment decision value is a moment value less than the absolute peak moment which can indicate that the moment is declining, taking into account possible noise at the peak moment. In FIG. 7, the buffer value is set to be 25 counts less than the peak moment or 95% of the peak value, but can be adjusted during an initial setup of the prosthetic joint 100. Thus, when the moment data indicates that the peak moment has been reached and that the moment is less 25 counts of the peak moment, or is 95% of the peak moment, the state controller 112 progresses to the next state, the Wait for Trigger 2 (phase 6) state. The declining peak moment decision value allows for some variations in moment data at the peak moment due to noise without the prosthetic joint 100 prematurely entering the next state. There are no additional exits for the Wait for Peak (phase 5) state.

Wait for Trigger 2 (Phase 6):

In the Wait for Trigger 2 state, the state controller waits until the moment data indicates that the moment is less than a declining moment decision value T2, which is indicated by the line 136 in FIG. 6. The declining moment decision value T2 is set relatively low compared to the peak moment to ensure that weight is removed from a prosthetic foot connected to the prosthetic joint 100. This is because in the Triggered (or Swing) (phase 7) state, the state controller 112 energizes the solenoid 108 causing the prosthetic joint 100 to be loose. Thus, in the Wait for Trigger 2 (phase 6) state, the state controller 112 ensures that the prosthetic joint 100 is not loose prematurely, such as before weight is removed from the prosthetic foot. Otherwise, the amputee can feel the loosening of the prosthetic joint 100, causing an abnormal and strange sensation for the amputee. Once the moment data indicates that the moment is less than the moment decision value T2, the state controller 112 advances the state of the prosthetic joint 100 to the next state, the Triggered (or Swing) (phase 7) state. In addition, the Wait for Trigger 2 (phase 6) state can also exit to the Wait for Extend (phase 1) state when the Not Loaded condition is reached. The Wait for Trigger 2 (phase 6) state can also exit to the Wait for Extend (phase 1) state when the Ramp Mode is Enabled.

Figure 8:
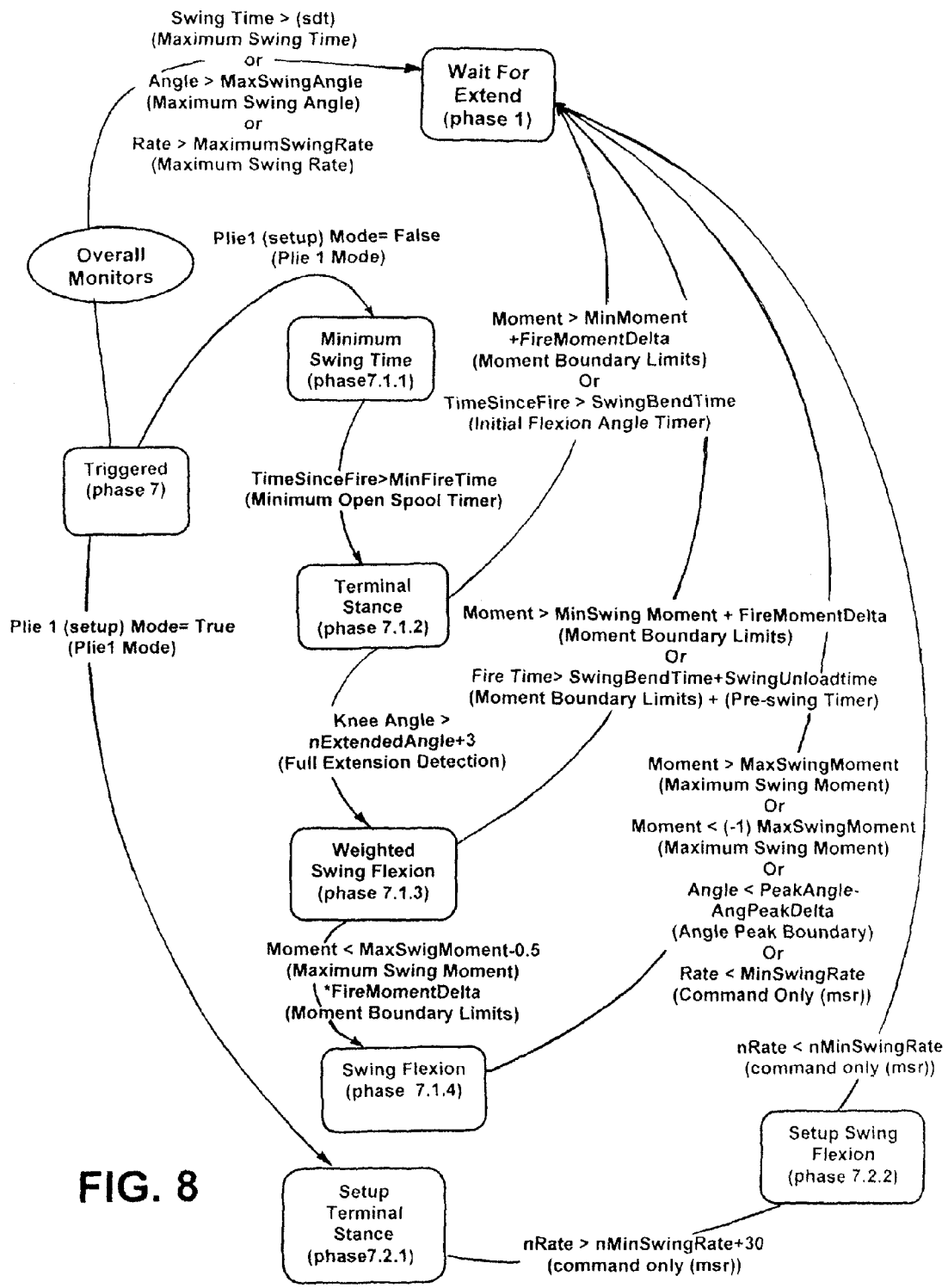
FIG. 8 a flowchart of states of a prosthetic joint according to an embodiment of the present invention.
Figure 9:
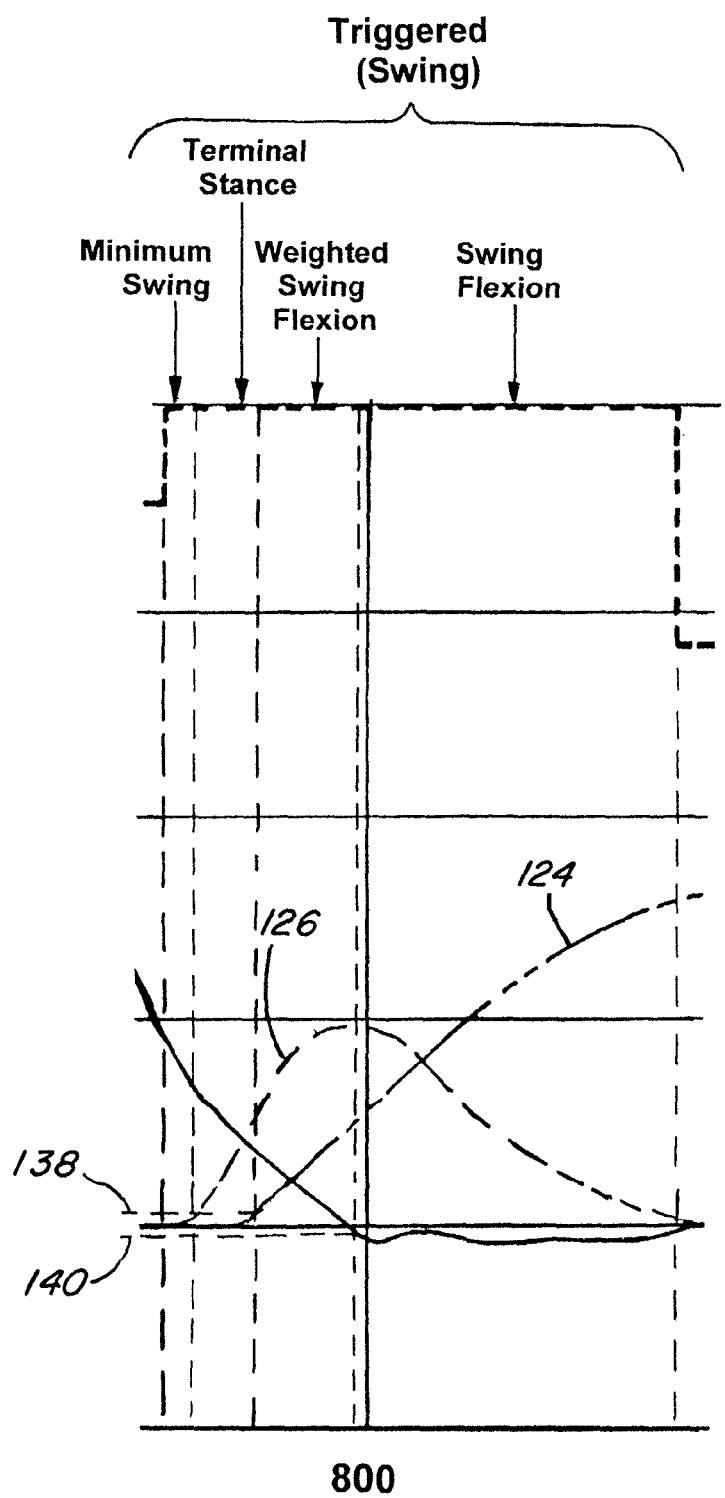
FIG. 9 is a portion of a graph of sagittal plane moment data, knee angle data, and knee angle rate of change data for an exemplary gait cycle and corresponding states of a prosthetic joint according to an embodiment of the present invention.

Triggered (or Swing) (Phase 7):

In the Triggered (or Swing) (phase 7) state, the state controller 112 will energize the solenoid 108 causing the prosthetic joint 100 to loosen. The state controller 112 continues to progress through several additional states while the solenoid 108 is energized to ensure that the prosthetic joint 100 transitions back to the stiff mode at the proper time. This can be seen, for example, in FIG. 8 and FIG. 9. FIG. 8 represents a flowchart of the Triggered (or Swing) (phase 7) state, while FIG. 9 is a graph of the relevant portion of the graph in FIG. 6 relating to the Triggered (or Swing) (phase 7) state.

As can be seen, the Triggered (or Swing) (phase 7) state includes various other states such as the sub-states including, Minimum Swing Time (phase 7.1.1) state, Terminal Stance (phase 7.1.2) state, Weighted Swing Flexion (phase 7.1.3) state, Swing Flexion (phase 7.1.4) state, Setup Terminal Stance (phase 7.2.1) state, and/or Setup Swing Flexion (phase 7.2.2) state. The Setup Terminal Stance (phase 7.2.1) state and/or the Setup Swing Flexion (phase 7.2.2) state are only entered when the prosthetic joint 100 is in a setup mode.

During the Triggered (or Swing) (phase 7) state, the state controller 112 provides additional monitoring as indicated by the oval labeled "Overall Monitors." The Overall Monitors monitor the swing time of the leg portion of the prosthetic joint 100, the knee angle of the prosthetic joint 100 and/or the knee angle rate of change of the prosthetic joint 100 even during the sub-states of the Triggered (or Swing) (phase 7) state. Thus, the state controller 112 constantly monitors the swing time data of the leg portion of the prosthetic joint 100, the knee angle data of the prosthetic joint 100, and/or the knee angle rate of change data of the prosthetic joint 100 to ensure that it does not exceed a maximum leg swing time, a maximum knee angle, and/or a maximum knee angle rate of change. This ensures that the prosthetic joint 100 is performing a normal gait instead of an abnormal gait.

For example, the maximum leg swing time ensures that the amputee does not take too long to swing the leg portion of the prosthetic joint 100. If the amputee takes too long, it is likely that there is problem in the gait of the amputee and that the state controller 112 should stiffen the prosthetic joint 100. The maximum knee angle ensures that the prosthetic joint 100 is not bent too much. If the prosthetic joint 100 is bent too much, it is likely that the user is falling or experiencing some other abnormal condition in the gait. In which case, the prosthetic joint 100 should be stiff. The maximum knee angle rate of change ensures that the prosthetic joint 100 is not bending too fast. Again if the prosthetic joint 100 is bending too fast, then the user is likely falling or experiencing some other abnormal condition in the gait and the prosthetic joint 100 should be stiff. Thus, should the leg swing time data indicate that the swing time exceeds the maximum leg swing time, the knee angle data indicate that the knee angle exceeds the maximum knee angle, and/or the knee angle rate of change data indicate that the knee angle rate of change exceeds the maximum knee angle rate of change, the state controller 112 proceeds to the Wait for Extend (phase 1) state.

In one embodiment, the sdt value corresponds to the maximum leg swing time, the MaxSwingAngle value corresponds to the maximum knee angle, and/or the MaximumSwingRate value corresponds to the maximum knee angle rate of change. The sdt value can be set by default to 225 ms, or to any other appropriate value.

The state controller 112 maintains a triggered state time counter indicating the time that the prosthetic joint 100 has been in the Triggered (phase 7) state. The triggered state time counter can begin as soon as the prosthetic joint 100 is in the Triggered (phase 7) state, or when the prosthetic joint 100 begins the Minimum Fire (Swing) Time (phase 7.1.1) state. The triggered state time counter, will be used, for example, in one or more of the states described below.

Minimum Fire (Swing) Time (Phase 7.1.1):

When the prosthetic joint 100 is in the Minimum Fire (Swing) Time state, the state controller 112 waits for a period of time before proceeding to the next state. Thus, the Minimum Fire (Swing Time) state provides a time delay during which perturbations in the moment caused by the transition into swing will not cause an abort from swing. For example, the Minimum Fire (Swing) Time (phase 7.1.1) state allows the sensor 114 to "settle" so that valid data is provided. It is purely time based and the value is set by a time delay value such as a minimum swing state time delay. The minimum swing time state delay is indicated in FIG. 8 as the MinFireTime. In one embodiment, the minimum swing time state delay MinFireTime can be set to 30 ms, but can be changed as necessary. There are no abnormal exits to the Wait for Extend (phase 1) state from the Minimum Fire (Swing) Time (phase 7.1.1) state. Thus, the state controller 112 can compare the triggered state time counter to the minimum swing time state delay MinFireTime and when the triggered state time counter exceeds the minimum swing time state delay MinFireTime, the state controller 112 sets the state of the prosthetic joint 100 to the Terminal Stance (phase 7.1.2) state.

Terminal Stance (Phase 7.1.2):

In the Terminal Stance (phase 7.1.2) state, the prosthetic joint 100 begins to bend. Thus, when the prosthetic joint 100 is in the Terminal Stance (phase 7.1.2) state, the state controller 112 looks for the prosthetic joint 100 to begin flexion. The state controller 112 proceeds to the next state, the Weighted Swing Flexion (phase 7.1.3) state, when the knee angle data indicates that the knee angle of the prosthetic joint 100 is greater than the bent knee angle decision value ExtendedAngle+3.

While in the Terminal Stance (phase 7.1.2) state, the state controller 112 monitors both the moment data and the time since the prosthetic device is in the Terminal Stance (phase 7.1.2) state. The knee angle data must indicate that the knee angle is greater than the bent knee angle decision value ExtendedAngle+3 before a bent knee time decision value, such as SwingBendTime value, is reached. This indicates that the prosthetic joint 100 is bent past a desired angle and is thus substantially beginning to bend. If the knee angle is not greater than the bent knee decision value ExtendedAngle+3 before the bent knee time decision value indicated by the SwingBendTime value is reached, then the amputee is taking too long to bend the prosthetic joint 100. This can indicate, for example, that the amputee is standing on his or her toes, has tripped, has stumbled, or is otherwise having an abnormal gait event. Thus, the state controller 112 will exit to the Wait for Extend (phase 1) state and return the prosthetic joint 100 to the stiff mode.

Furthermore, if the moment data indicates a large moment such as one greater than a first moment boundary value indicated by the lowest moment detected (MinMoment) plus a moment noise buffer value to account for noise (FireMomentDelta), then the state controller 112 exits to the Wait for Extend (phase 1) state and return the prosthetic joint 100 to the stiff mode. This is because a large moment at this state indicates that the amputee is standing on his or her toes, has tripped, has stumbled, or is otherwise having an abnormal gait.

Weighted Swing Flexion (Phase 7.1.3):

In the Weighted Swing Flexion (phase 7.1.3) state, the state controller 112 monitors the moment data to ensure that the moment of the prosthetic joint is decreasing. Thus, the state controller 112 determines whether the moment data indicates that the moment is less than a second moment boundary value or not. The second moment boundary value is the maximum swing moment value indicated as MaxSwingMoment in FIG. 8 minus 50% of the moment noise buffer value FireMomentDelta. The maximum swing moment value MaxSwingMoment is the maximum moment allowable during a swing phase of the prosthetic joint 100. Ideally there would be little to no moment during swing and therefore the maximum swing moment value MaxSwingMoment can be set to a low value. When the state controller 112 determines that the moment data indicates that the moment is less than the second moment boundary value, the state controller 112 sets the state of the prosthetic joint 100 to the next state, the Swing Flexion (phase 7.1.4) state. The second moment boundary value is indicated by line 140 in FIG. 9.

While in the Weighted Swing Flexion (phase 7.1.3) state, the state controller 112 monitors both the moment data and the triggered state time counter. The moment data must indicate that the moment is less than the second moment boundary value before the triggered state time counter exceeds a decreased moment time decision value. The decreased moment time decision value can include, for example, the SwingBendTime value disclosed above in addition to another time value, a decreasing moment time buffer value SwingUnloadTime to compensate for the time that the amputee should have from bending the prosthetic joint 100 to decreasing the moment of the prosthetic joint 100. Thus, the amputee only has a certain amount of time to decrease the moment below the second moment boundary value in order for the gait to be considered a normal gait. If the triggered state time counter exceeds the decreased moment time decision value, then the state controller 112 exits to the Wait for Extend (phase 1) state and returns the prosthetic joint 100 to the stiff mode.

Furthermore, if the moment data indicates that the moment is greater than a third moment boundary value, then the moment is not decreasing according to a normal gait. In such a case, the state controller 112 exits to the Wait for Extend (phase 1) state and instructs the prosthetic joint 100 to remain stiff. The third moment boundary value includes the sum of a minimum swing moment boundary indicated in FIG. 8 as a MinSwingMoment, and the moment noise buffer FireMomentDelta.

Swing Flexion (Phase 7.1.4):

When the prosthetic joint 100 is in the Swing Flexion (phase 7.1.4) state, all exits are to the Wait for Extend (phase 1) state. A first exit occurs when the knee angle rate of change of the prosthetic joint 100 falls below a minimum knee angle rate of change MinSwingRate. This indicates that the knee has nearly stopped bending and is beginning to straighten as the lower leg swings forward. This is the exit that occurs during a normal step. Another exit to the Wait for Extend (phase 1) state occurs when the moment data indicates that the moment exceeds the bounds of zero plus or minus the maximum swing moment value MaxSwingMoment. This indicates that there is increased pressure on the prosthetic foot connected to the prosthetic joint 100. Thus, the prosthetic joint 100 should be stiff. Finally the state controller 112 determines whether the knee angle is less than the peak angle by a value of an angle peak noise buffer AngPeakDelta. Should the angle drop below the peak angle by the angle peak noise buffer AngPeakDelta the state controller 112 sets the state of the prosthetic joint 100 to the Wait for Extend (Stance) (phase 1). This is because the knee angle indicates that the knee has finished bending and is beginning to extend in anticipation of putting pressure on the prosthetic foot and/or the prosthetic joint 100. Thus, the prosthetic joint 100 should be stiff.

In FIG. 8, the Setup Terminal Stance (phase 7.2.1) state, and the Setup Swing Flexion (phase 7.2.2) state are entered when the prosthetic joint 100 is in the setup mode. Thus, the other states, Minimum Swing Time (phase 7.1.1) state, Terminal Stance (phase 7.1.2) state, Weighted Swing Flexion (phase 7.1.3) state, Swing Flexion (phase 7.1.4) state are bypassed in the setup mode. The Setup Terminal Stance (phase 7.2.1) state, and the Setup Swing Flexion (phase 7.2.2) state are designed to provide minimal stumble recovery and to allow operation of the optimization unit 110 to collect a plurality of data files related to normal steps of an amputee to optimize the adjustable parameters of the prosthetic joint 100.

The adjustable parameters can include, for example, the prosthetic joint movement decision values such as the straight knee angle decision value (ExtendedAngle−3), the bent knee angle decision value (ExtendedAngle+3), the extend wait state time delay (ExtendHoldDelay), the heel moment decision value (HeelMinMax), rising moment decision value (T1), wait for trigger 1 state count (MaxHeelWait), declining peak moment decision value (PeakMoment−25 or PeakMoment*0.95), declining moment decision value (T2), maximum leg swing time (sdt), maximum knee angle (MaxSwingAngle), maximum knee angle rate of change (MaximumSwingRate), minimum swing state time delay (MinFireTime), bent knee time decision value (SwingBendTime), first moment boundary value (MinMoment+FireMomentDelta), moment noise buffer value (FireMomentDelta), second moment boundary value (MaxSwingMoment+FireMomentDelta), maximum swing moment value (MaxSwingMoment), decreased moment time decision value (SwingBendTime+SwingUnloadTime), decreased moment time buffer value (SwingUnloadTime), third moment boundary value (MinSwingMoment+FireMomentDelta), minimum swing moment boundary (MinSwingMoment), maximum swing moment (MaxSwingMoment), angle peak noise buffer value (AngPeakDelta), and/or the minimum knee angle rate of change value (MinSwingRate).

In the setup mode, the prosthetic joint 100 should not prematurely exit into the Wait for Extend (phase 1) state because the amputee is taking normal steps under the supervision of another person, and is not stumbling. Thus, there is no need to predict when the amputee is stumbling or is having an abnormal gait because it is assumed that the amputee is taking normal steps. Thus, the prosthetic joint 100 should only exit into the Wait for Extend (phase 1) state at the end of a normal step instead of prematurely due to a perceived abnormal step.

By adjusting the prosthetic joint movement decision values, the prosthetic joint 100 can minimize an amount of times that the prosthetic joint 100 exits one of the states into the Wait for Extend (phase 1) state, while also providing a more accurate assessment of when the prosthetic joint 100 should exit to the Wait for Extend (phase 1) state. In both the Setup Terminal Stance (phase 7.2.1) state, and the Setup Swing Flexion (phase 7.2.2) state, the Overall Monitors can remain active in case when attempting a normal step, the amputee truly has an abnormal gait such as stumbling or falling.

Setup Terminal Stance (Phase 7.2.1):

This state is entered immediately when in Setup Mode and the Triggered state (phase 7) state is entered. The Setup Terminal Stance (phase 7.2.1) ensures that a knee angle rate of change of the prosthetic joint 100 exceeds the minimum knee angle rate of change value MinSwingRate+30. This ensures that the prosthetic joint 100 is in flexion and is bending before the state controller loosens the prosthetic joint 100 in the Setup Swing Flexion (phase 7.2.2) state.

Setup Swing Flexion (Phase 7.2.2):

This state represents swing flexion. In the Setup Swing Flexion (phase 7.2.2) state, the only and normal exit is to the Wait For Extend (phase 1) state and happens when the knee angle rate of change of the prosthetic joint 100 is less than the minimum knee angle rate of change MinSwingRate.

Figure 10:
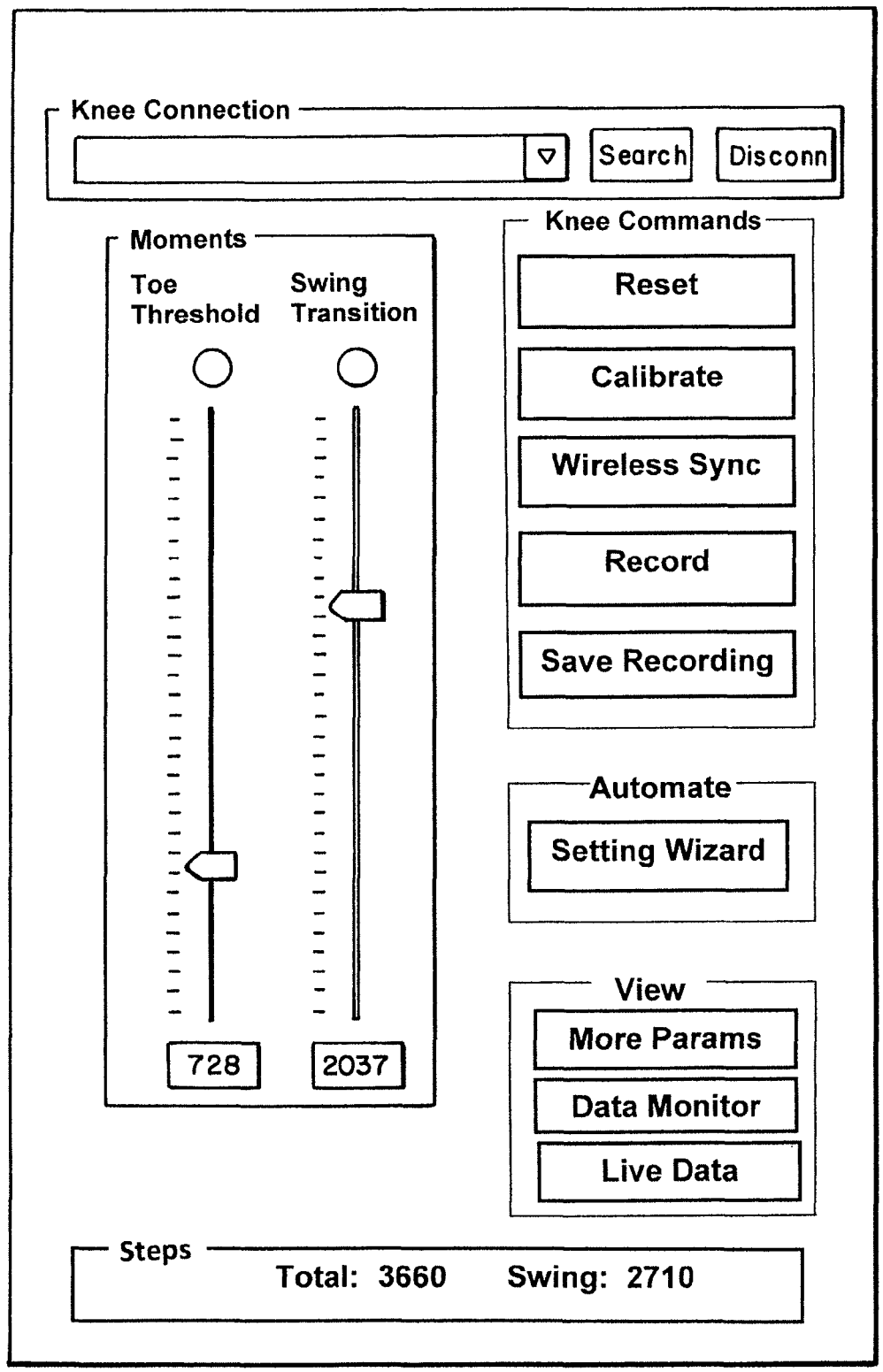
FIG. 10 depicts information displayed by an optimization unit according to an embodiment of the present invention.
Figure 11:
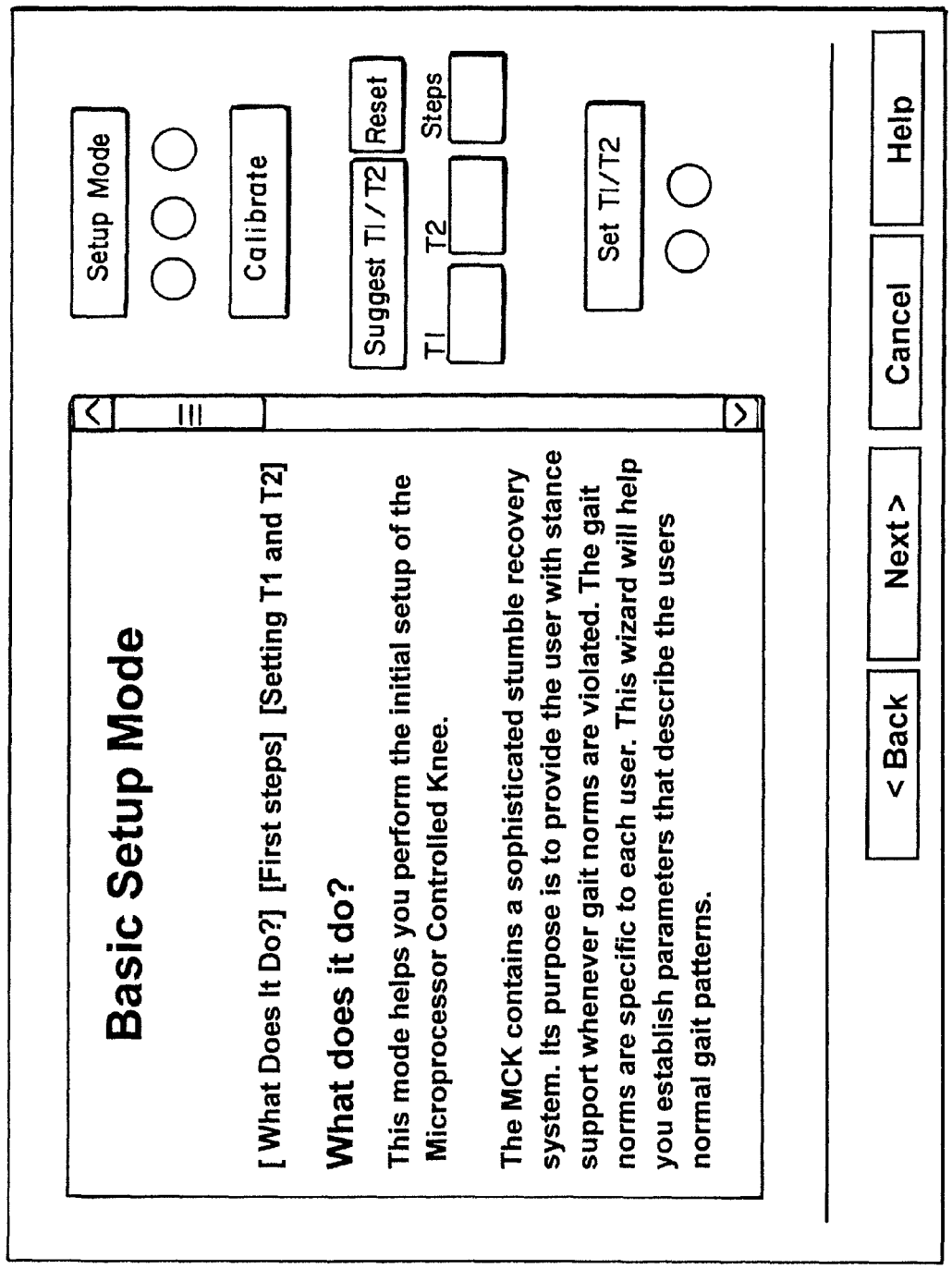
FIG. 11 depicts information displayed by an optimization unit according to an embodiment of the present invention.

FIG. 10 can be, for example, a screen provided by the optimization unit 110. To enter the setup mode, the user can select the "Setting Wizard." As seen in FIG. 11, the optimization unit can then enter into a basic setup mode to optimize the prosthetic joint movement decision values. To optimize the prosthetic joint movement decision values, the optimization unit 110 will collect a plurality of data files of a user walking at different speeds.

Figure 12:
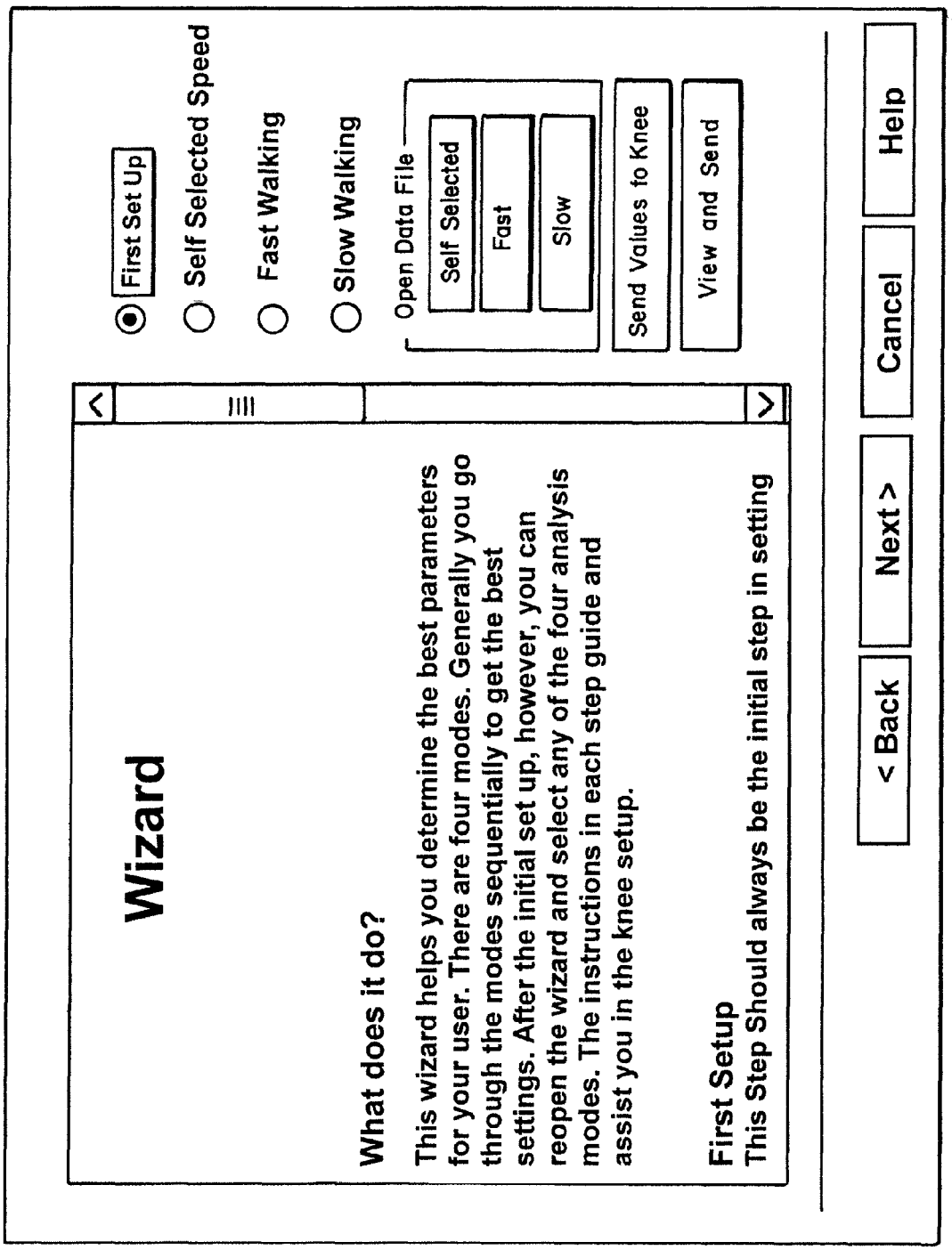
FIG. 12 depicts information displayed by an optimization unit according to an embodiment of the present invention.

As seen in FIG. 12, the optimization unit 110 can collect a data file for a user walking at a fast speed, a data file for a user walking at a slow speed, and/or a data file for a user walking at a self selected normal speed. Although the optimization unit 110 can utilize just a single data file, it is preferable that multiple data files are used with the user walking at different speeds to ensure that the prosthetic joint movement decision values are optimized not only for a single walking speed of the user, but for multiple walking speeds. In one embodiment, the optimization unit 110 can collect a data file for a user walking at a first speed, a data file for a user walking at a second speed faster than the first speed, and/or a data file for a user walking at a third speed faster than the second speed.

Figure 13:
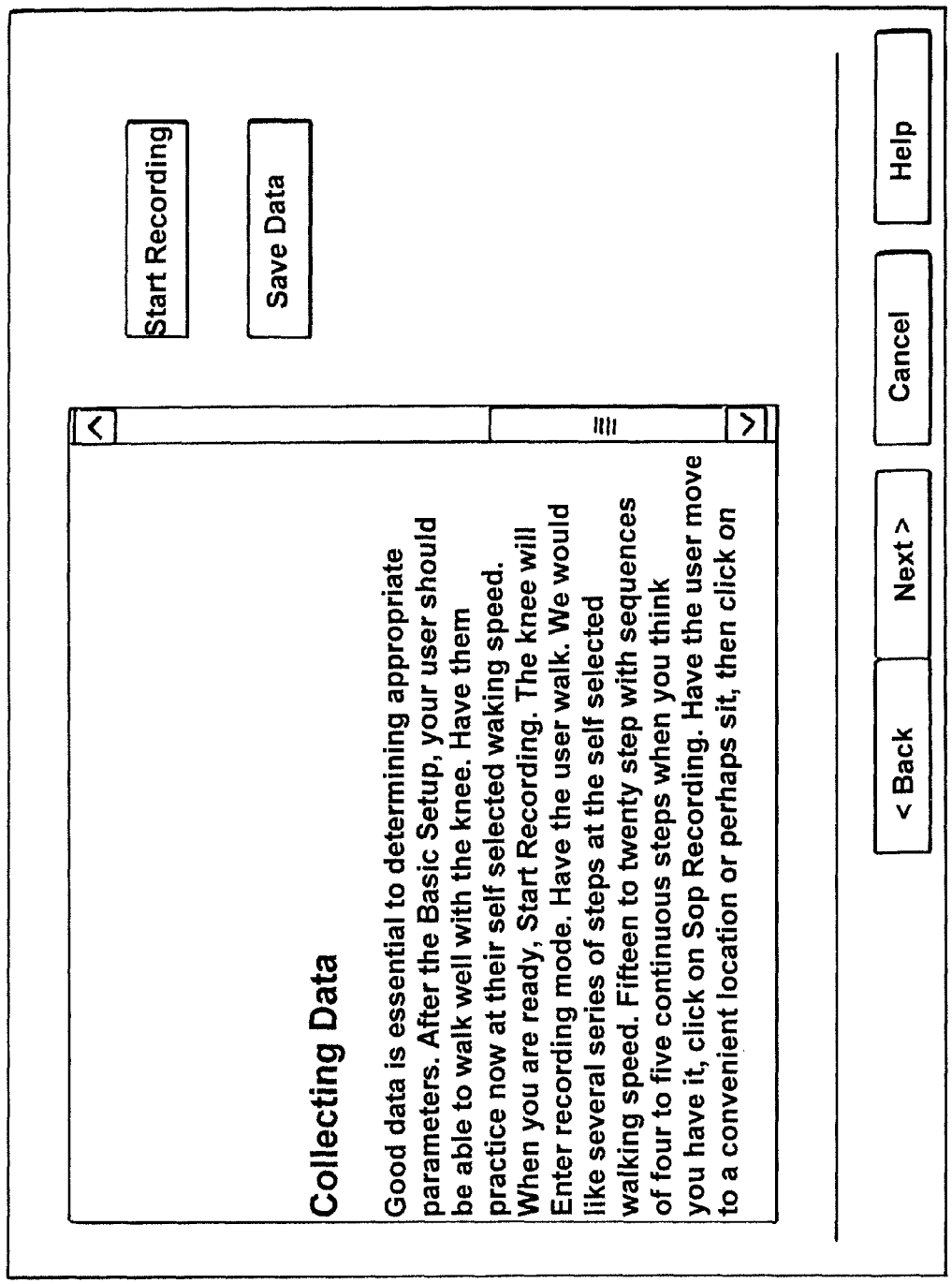
FIG. 13 depicts information displayed by an optimization unit according to an embodiment of the present invention.
Figure 14:
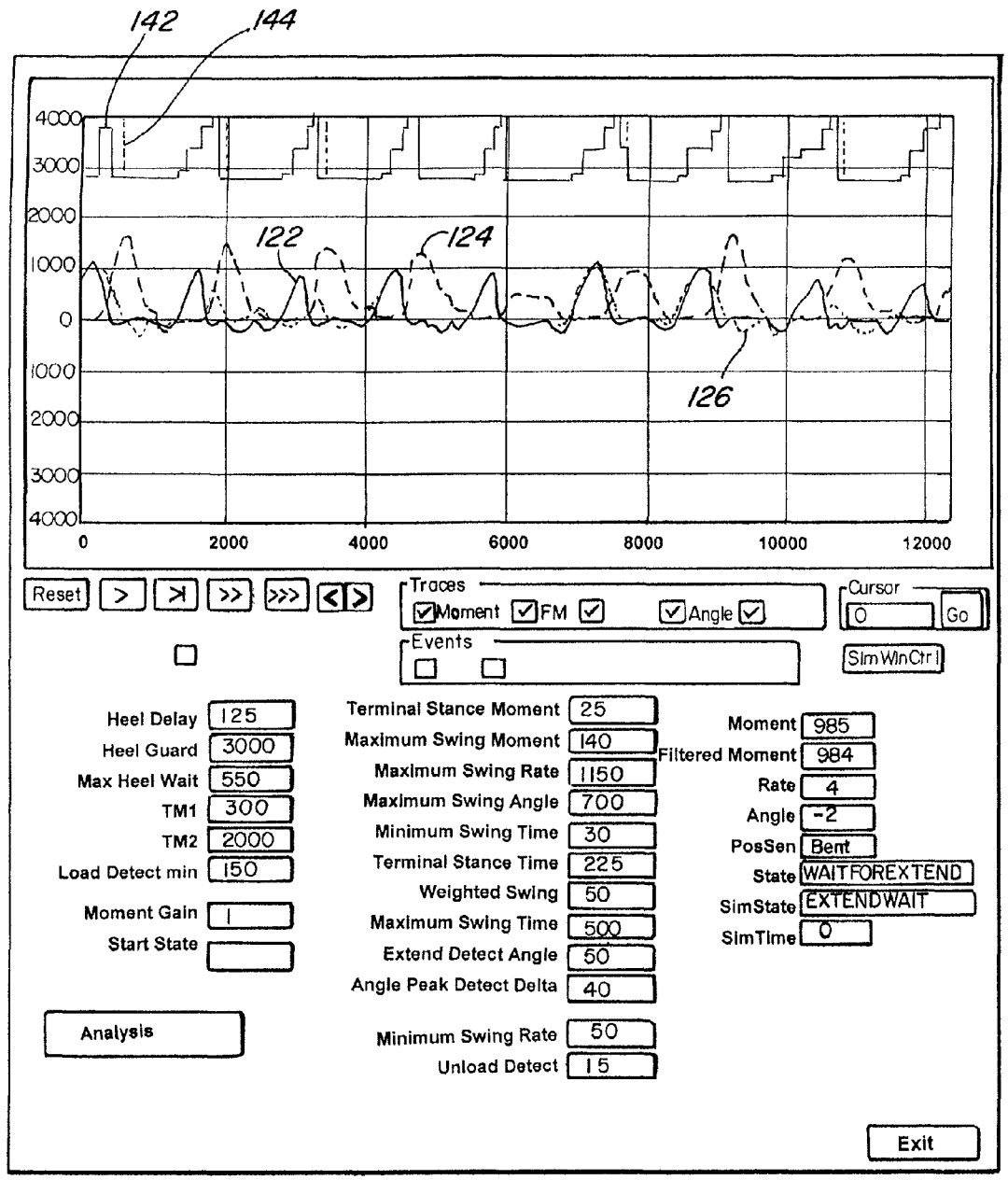
FIG. 14 depicts data collected by an optimization unit according to an embodiment of the present invention.

As seen in FIG. 13, to start collecting a data file, a user can select the "Start Recording" button. As seen in FIG. 14, information for a single data file can be displayed including the moment data indicated by the curve 122, the knee angle data indicated by the curve 124, the knee angle rate of change data indicated by the curve 126, and/or the state data indicated by the curve 142. To optimize the prosthetic joint movement decision values, the optimization unit 110 analyzes the state data to ensure that the state of the prosthetic device cycles normally and that there are no abnormal exits to the Wait for Extend (phase 1) state. If there is an abnormal exit, the optimization unit 110 adjusts the relevant prosthetic joint movement decision value so that the state of the prosthetic joint 100 does not exit to the Wait for Extend (phase 1) state. Again, this is because the user is walking normally throughout the single data file. Thus, any exits to the Wait for Extend (phase 1) state is considered to be premature and should be minimized if possible.

The optimization unit 110 can iteratively analyze the single data file to adjust the prosthetic joint movement decision values until the number of times the state prematurely exits to the Wait for Extend (phase 1) state is minimized. A similar reiterative analysis can be performed for the other data files either serially or in parallel. When the prosthetic joint movement decision values are adjusted, the simulator state data 144 can be displayed to indicate the state of the prosthetic joint 100 with the adjusted prosthetic joint movement decision values.

Furthermore, in one embodiment, the optimization unit 110 can also adjust the relevant prosthetic joint movement decision values to ensure that the state of the prosthetic joint 100 correctly corresponds to the particular portion of the gait that the amputee is in. For example, in reference to FIG. 5, if the prosthetic joint 100 is in the Extend Wait (phase 2) state when the user is still in the Terminal Swing portion of the gait cycle, then the corresponding prosthetic joint movement decision values can be adjusted to ensure that the prosthetic joint 100 is in the Wait for Extend (phase 1) state.

Figure 15:
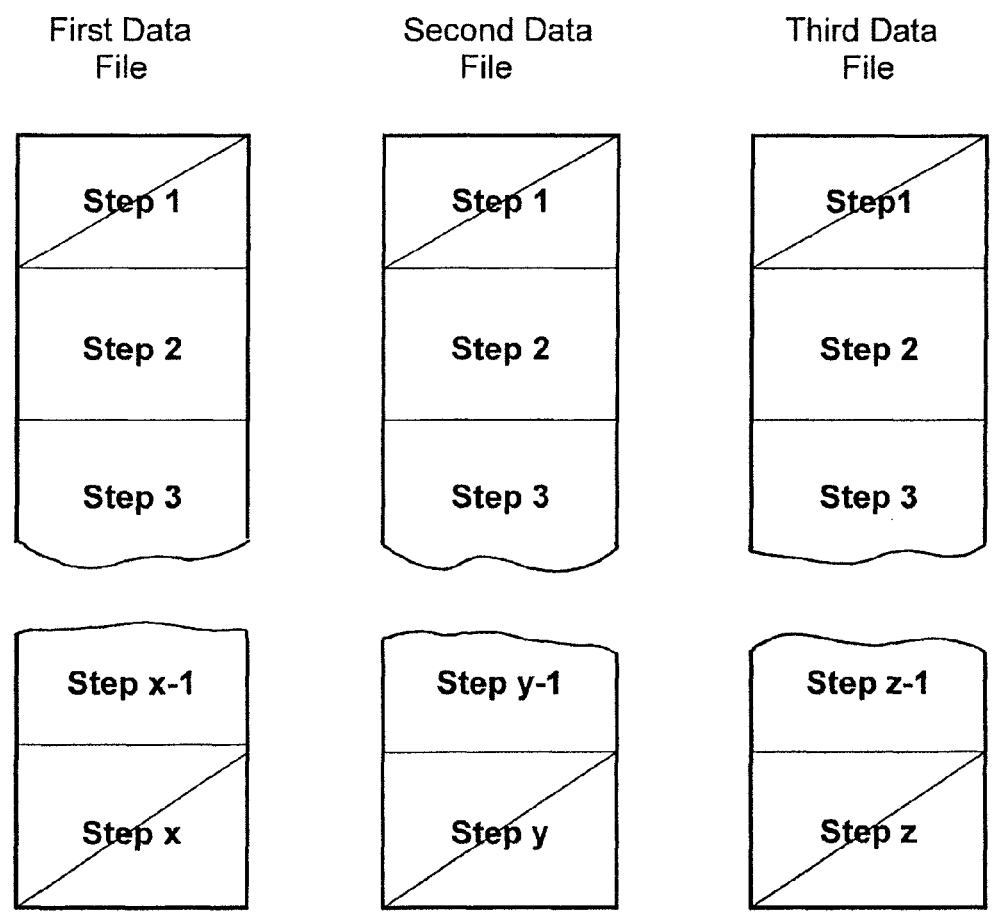
FIG. 15 depicts a plurality of data files used by an optimization unit according to an embodiment of the present invention.

To collect information for the data files, the user should take a plurality of steps as shown in FIG. 15. As seen in FIG. 15, in the first data file the user has taken "x" steps, in the second data file the user has taken "y" steps, and in the third data file the user has taken "z" steps. The optimization unit 110 collects data for the "x" steps, the "y" steps, and the "z" steps, but filters out information regarding the first step and the last step. This is because those steps tend to be more abnormal and not necessarily the steps the user will normally take. This helps to ensure that the data used to optimize the prosthetic joint movement decision values are correct. In one embodiment, "x," "y," and "z" are selected be greater than 22 to ensure that at least 20 steps are recorded for each data file. Of course "x," y," and "z," can be set to any value to ensure that reliable information is captured for optimization of the prosthetic joint movement decision values.

Figure 16:
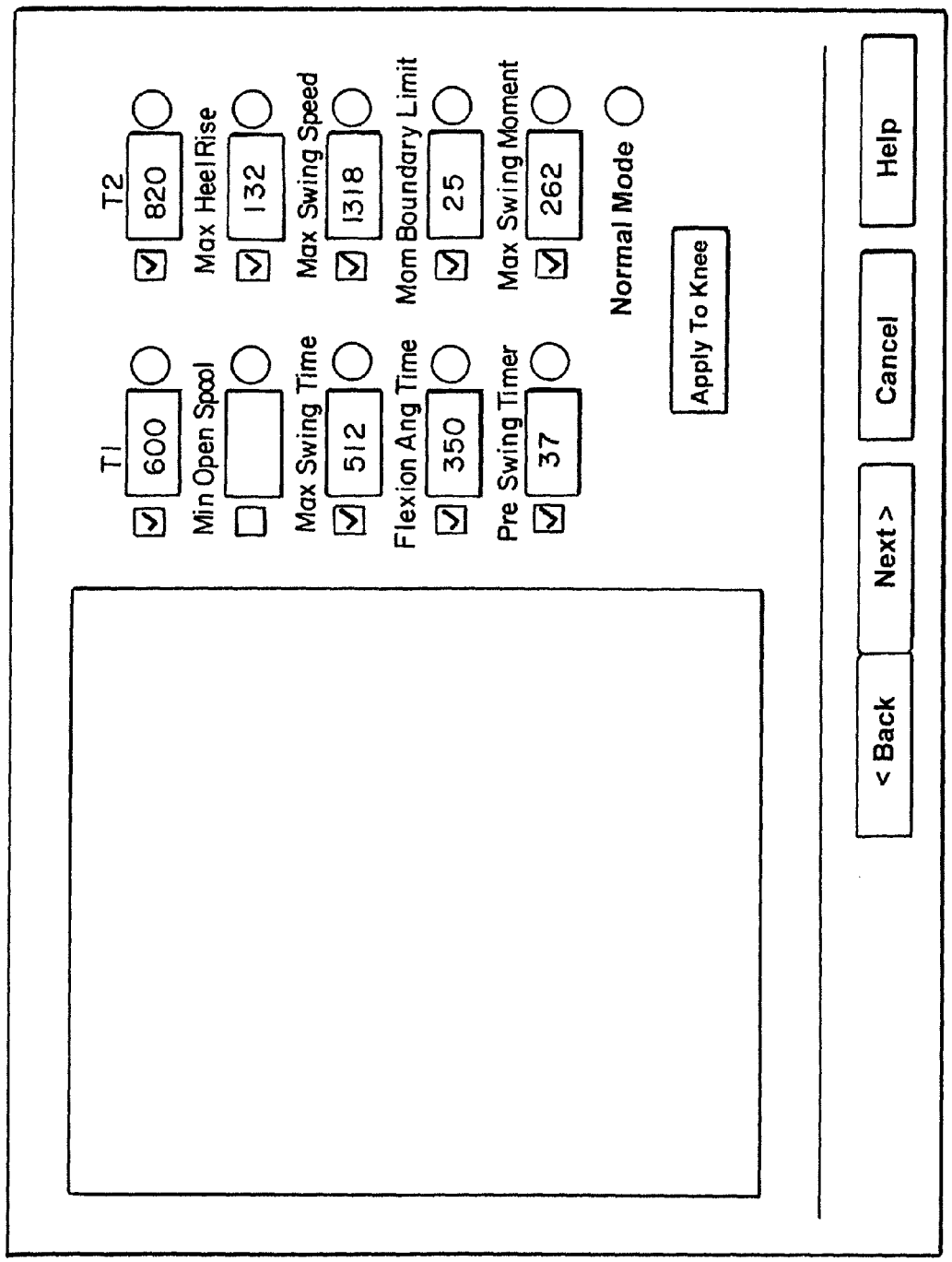
FIG. 16 depicts suggested prosthetic joint movement decision values by an optimization unit according to an embodiment of the present invention.

As seen in FIG. 16, after the optimization unit 110 has finished analyzing the data files and adjusting the prosthetic joint movement decision values, it can display the suggested values for the prosthetic joint movement decision values. The user can then choose to apply the prosthetic joint movement decision values that have been optimized or retain the original prosthetic joint movement decision values.

Thus, the optimization unit 110 can adjust the numerous prosthetic joint movement decision values without much human intervention or interaction. Given the current number of prosthetic joint movement decision values and the possibility that such numbers will increase, this can reduce the cost of fine tuning the prosthetic joint 100 and its corresponding prosthetic device. The optimization unit 110 can allow the prosthetic joint 100 to function to its full capacity in a cost effective manner. Furthermore, the optimization unit 110 allows a variety of people to set up the prosthetic joint 100 and its corresponding prosthetic device. With its ease of use, users without advanced degrees or significant experience in the industry may be capable of setting up the prosthetic joint 100 and its corresponding prosthetic device. This can further reduce the costs associated with the prosthetic joint 100 and its corresponding prosthetic device.

In one embodiment, state transitions identified by the optimization unit 100 are depicted in FIG. 17. The optimization unit 110 can communicate, for example, with the prosthetic joint 100 in a wired or wireless manner. The optimization unit 110 can also be part of a computer or a handheld system.

Figure 18:
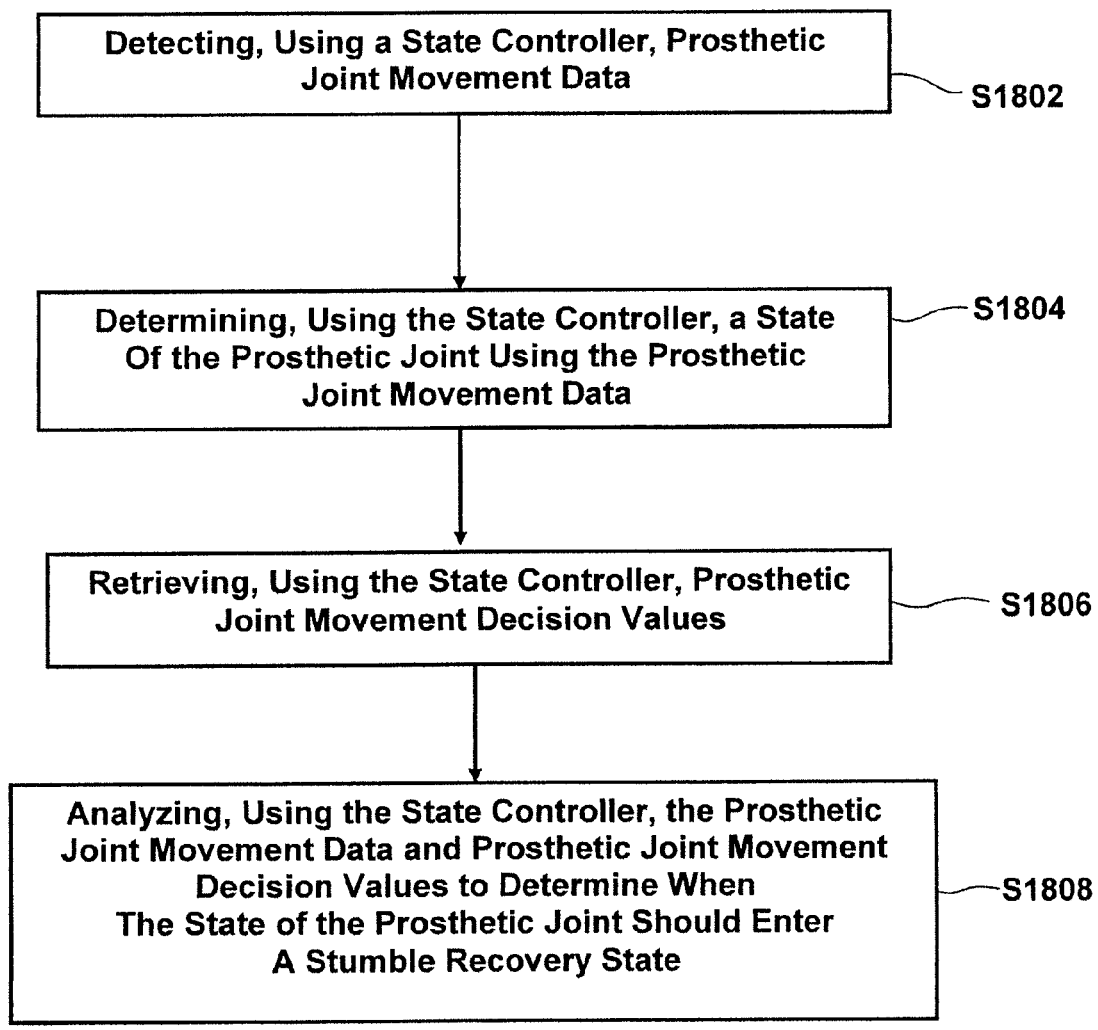
FIG. 18 depicts a process according to an embodiment of the present invention.

In one embodiment, the present invention can include a process as shown in FIG. 18. In Step S1802, prosthetic joint movement data can be detected. For example, the state controller 112 (FIG. 4) can detect prosthetic joint movement data such as swing time data, moment data, knee angle data, and/or knee angle rate of change data. In Step S1804, a state of the prosthetic joint can be determined using a state controller and the prosthetic joint movement data. For example, the state controller 112 can determine a state of the prosthetic joint 100 using the prosthetic joint movement data.

In Step S1806, the prosthetic joint movement decision values can be retrieved using a state controller. For example, the state controller 112 can retrieve the prosthetic joint movement decision values from the memory 116. In Step S1808, the prosthetic joint movement data and the prosthetic joint movement decision values are analyzed using the state controller to determine when the state of the prosthetic joint should enter a stumble recovery state. For example, the state controller 112 analyzes the prosthetic joint movement data and the prosthetic joint movement decision values stored in the memory 116 to determine when the state of the prosthetic joint should enter a stumble recovery state.

Figure 19:
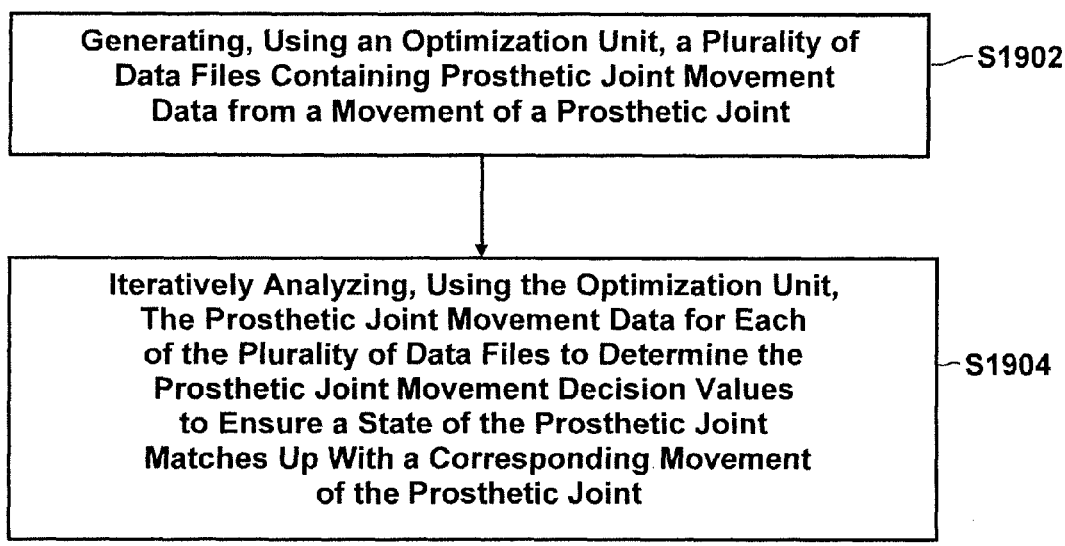
FIG. 19 depicts a process according to an embodiment of the present invention.

In another embodiment, the present invention can include a process shown in FIG. 19. In Step S1902, an optimization unit can be used to generate a plurality of data files containing prosthetic joint movement data from a movement of the prosthetic joint. For example, the optimization unit 110 can be used to generate a plurality of data files containing joint movement data of an amputee walking at various speeds.

In Step S1904, the optimization unit can iteratively analyze the prosthetic joint movement data for each of the plurality of data files to determine the prosthetic joint movement decision values to ensure a state of the prosthetic joint matches with a corresponding movement of the prosthetic joint. For example, the optimization unit 110 can iteratively analyze the prosthetic joint movement data for each of the plurality of data files and adjust the prosthetic joint movement decision values to ensure a state of the prosthetic joint matches up with a corresponding movement of the prosthetic joint. This can prevent, for example, the prosthetic joint 100 from prematurely entering a stumble recovery state.

In one embodiment, instead of a binary operation, the hydraulic damping cylinder 102 (FIG. 1), and the actuator 150 can also operate not just in a loose mode and a stiff mode, but also one in various other modes with varied resistances. Thus, there could also be a middle mode, which has a resistance between a low resistance and a high resistance, or any other number of modes with resistances between the low resistance and the high resistance.

The process described above can be stored in a memory of a computer system as a set of instructions to be executed. In addition, the instructions to perform the processes described above could alternatively be stored on other forms of non-transitory machine-readable media, including magnetic and optical disks and related media. For example the processes described could be stored on machine-readable media, such as magnetic disks or optical disks, which are accessible via a disk drive (or computer-readable medium drive). Further, the instructions can be downloaded into a computing device over a data network in a form of compiled and linked version.

Alternatively, the logic to perform the processes as discussed above could be implemented in additional computer or machine readable media, such as discrete hardware components as large-scale integrated circuits (LSI's), application-specific integrated circuits (ASIC's), firmware such as electrically erasable programmable read-only memory (EEPROM's); and electrical, optical, acoustical and other forms of propagated signals (e.g., carrier waves, infrared signals, digital signals, etc.).

In one aspect, the control system within prosthetic knee 1o includes at least one central processing unit (CPU) or processor. The CPU can be coupled to a memory, ROM, or machine-readable media containing the computer-executable instructions for operating the valve of prosthetic knee 1o. Machine-readable media can be any available media that can be accessed by the system and includes both volatile and non-volatile media, removable and non-removable media implemented in any method or technology for storage of information such as computer readable instructions, data structures, program modules or other data. Machine storage media includes, but is not limited to, RAM, ROM, EEPROM, flash memory, portable memory, or other memory technology, CD-ROM, digital versatile disks (DVD), or other optical disk storage, magnetic cassettes, magnetic tape, magnetic disk storage or other magnetic storage devices, or any other medium which can be used to store the desired information and which can be accessed by the control system, including remote storage accessed over a wireless connection, such as Bluetooth or 802.11-type wireless communication signals. The machine-readable media may store instructions or data which implement all or part of the system described herein.

Communication media typically embodies machine-readable instructions, data structures, program modules, or other data in a modulated data signal such as a carrier wave or other transport mechanism and includes any information delivery media. By way of example, and not limitation, communication media includes wired media such as a wired network or direct-wired connection, and wireless media such as acoustic, RF, infrared, or other wireless media.

The present disclosure has been described above in terms of presently preferred embodiments so that an understanding of the present disclosure can be conveyed. However, there are other embodiments not specifically described herein for which the present disclosure is applicable. Therefore, the present disclosure should not to be seen as limited to the forms shown, which is to be considered illustrative rather than restrictive.

What is claimed is:

1. A prosthetic joint system capable of selectively entering a stumble recovery state, the prosthetic joint system comprising:
    a prosthetic joint; and
    a state controller coupled to the prosthetic joint and programmed to:
        detect prosthetic joint movement data;
        determine a state of the prosthetic joint using the prosthetic joint movement data; and
        analyze prosthetic joint movement data detected during an un-weighted state of a prosthetic foot connected to the prosthetic joint and at least one prosthetic joint movement decision value to determine when the state of the prosthetic joint should enter a stumble recovery state.

2. The prosthetic joint system of claim 1 wherein the prosthetic joint movement data detected during the un-weighted state of the prosthetic foot includes swing time data, moment data, knee angle data, or knee angle rate of change data.

3. The prosthetic joint system of claim 1 wherein the at least one prosthetic joint movement decision value includes a maximum leg swing time.

4. The prosthetic joint system of claim 1 wherein the at least one prosthetic joint movement decision value includes a maximum knee angle or a maximum knee angle rate of change.

5. The prosthetic joint system of claim 1 wherein the at least one prosthetic joint movement decision value includes a bent knee time decision value.

6. The prosthetic joint system of claim 1 wherein the at least one prosthetic joint movement decision value includes a moment boundary value and a decreased moment time decision value.

7. The prosthetic joint system of claim 1 wherein the at least one prosthetic joint movement decision value includes a bent knee angle decision value.

8. A method for controlling when a prosthetic joint enters a stumble recovery state, the method comprising:
    detecting, using a state controller, prosthetic joint movement data;
    determining, using the state controller, a state of the prosthetic joint using the prosthetic joint movement data;
    retrieving, using the state controller, at least one prosthetic joint movement decision value; and
    analyzing, using the state controller, prosthetic joint movement data detected during an un-weighted state of a prosthetic foot connected to the prosthetic joint and the at least one prosthetic joint movement decision value to determine when the state of the prosthetic joint should enter a stumble recovery state.

9. The method of claim 8 wherein the prosthetic joint movement data detected during the un-weighted state of the prosthetic foot includes swing time data, moment data, knee angle data, or knee angle rate of change data.

10. The method of claim 8 wherein the at least one prosthetic joint movement decision value includes a maximum knee angle or a maximum knee angle rate of change.

11. The method of claim 8 wherein the at least one prosthetic joint movement decision value includes a maximum leg swing time.

12. The method of claim 8 wherein the at least one prosthetic joint movement decision value includes a bent knee time decision value.

13. The method of claim 8 wherein the at least one prosthetic joint movement decision value includes a moment boundary value and a decreased moment time decision value.

14. The method of claim 8 wherein the at least one prosthetic joint movement decision value includes a bent knee angle decision value.

* * * * *